(12) United States Patent
Romo et al.

(10) Patent No.: US 7,230,021 B2
(45) Date of Patent: Jun. 12, 2007

(54) POTENT, SIMPLIFIED DERIVATIVES OF PATEAMINE A

(75) Inventors: Daniel Romo, College Station, TX (US); Jun Liu, Clarksville, MD (US); Nam Song Choi, College Station, TX (US); Zonggao Shi, Secane, PA (US)

(73) Assignee: The Texas A&M University System, College Station, TX (US)

( * ) Notice: Subject to any disclaimer, the term of this patent is extended or adjusted under 35 U.S.C. 154(b) by 333 days.

(21) Appl. No.: 10/388,257

(22) Filed: Mar. 13, 2003

(65) Prior Publication Data

US 2003/0216436 A1 Nov. 20, 2003

Related U.S. Application Data

(60) Provisional application No. 60/364,347, filed on Mar. 13, 2002.

(51) Int. Cl.
- C07D 245/00 (2006.01)
- C07D 277/00 (2006.01)
- A61K 31/425 (2006.01)
- A61K 31/415 (2006.01)
- A61P 37/00 (2006.01)

(52) U.S. Cl. ............... 514/368; 514/375; 514/393; 540/456; 540/460; 540/468; 548/201

(58) Field of Classification Search ............... 514/368, 514/375, 393; 540/456, 460, 468; 548/201
See application file for complete search history.

(56) References Cited

U.S. PATENT DOCUMENTS

| | | | | |
|---|---|---|---|---|
| 4,548,481 A | 10/1985 | Yamada | ............... | 350/559 |
| 4,729,996 A | 3/1988 | Wright et al. | ............... | 514/215 |
| 4,737,510 A | 4/1988 | Rinehart, Jr. | ............... | 514/388 |
| 4,808,590 A | 2/1989 | Higa et al. | ............... | 514/272 |
| 6,057,333 A | 5/2000 | Gunaskera et al. | ......... | 514/278 |

FOREIGN PATENT DOCUMENTS

EP 0 647 645 A1 4/1995

OTHER PUBLICATIONS

Hehre W., et al., Self-Consistent Molecular Orbital Methods. XII. Further Extensions of Gaussian-Type Basis Sets for Use in Molecular Orbital Studies of Organic Molecules, J. Chem. Phys., 56:2257-2261 (1972).
Inanaga J., et al., A Rapid Esterification by Means of Mixed Anhydride and Its Application to Large-ring Lactonization, Chem. Soc. Japan, 52:1989-1993 (1979).
Franci M., et al., Self-Consistent Molecular Orbital Methods. XXIII. A Polarization-Type Basis Set for Second-Row Elements, J. Chem. Phys 77:3654-3665 (1982).
Northcote P., et al., Pateamine: A Potent Cytotoxin From the New Zealand Marine Sponge, Mycale Sp., Tetrahedron Letters, vol. 32, No. 44, pp. 6411-6414 (1991).
Farina V., et al., Large Rate Accelerations in the Stile Reaction with Tri-2-furylphosphine and Triphenylarsine as Palladium Ligands: Mechanistic and Synthetic Implications, J. Am. Chem. Soc. 1991, 113, 9585-9595.
Becke, A., A New Mixing of Hartree-Fock and Local Density-Functional Theories, J. Chem. Phys. 98:1372-1377 (1993).
Becke, A., Density-Functional Thermochemistry. III. The Role of Exact Exchange, J. Chem. Phys. 98:5648-5652 (1993).
Aguilar, E., et al., Reinvestigation of a Modified Hantzch Thiazole Synthesis, Tetrahedron Letters, vol. 35, No. 16, pp. 2473-2476 (1994).
Su, B., et al. JNK Is Involved in Signal Integration During Costimulation of T Lymphocytes, Cell, vol. 77, 727-736 (1994).
Dong, Q., et al., Reductive Cleavage of TROC Groups Under Neutral Conditions with Cadmium-Lead Couple, Tetrahedron Letters, vol. 36, No. 32, pp. 5681-5682 (1995).
Hung, D., et al., Synthesis of Discodermolides Useful for Investigating Microtubule Binding and Stabilization, J. Am. Chem. Soc. 1996, 118, 11054-11080.
Hung, D., et al., Understanding and Controlling the Cell Cycle With Natural Products, Chemistry & Biology, Aug. 1996, 3:623-639.
Rzasa, R., et al., Total Synthesis of the Novel, Immunosuppressive Agent (-)-Pateamine A from Mycale sp. Employing a B-Lactam-Based Macrocyclization, J. Am. Chem. Soc. 1998, 120, 591-592.
Remuinan, M., et al., Total Synthesis of (-)-Pateamine, a Novel Polyene Bis-Macrolide with Immunosuppressive Activity From the Sponge Mycale sp., Tetrahedron Letters 41 (2000) 7367-7371.
Romo, D., et al., Total Synthesis and Immunosuppressive Activity of (-)-Pateamine A and Related Compounds: Implementation of B-Lactam-Based Macrocyclization, J. Am. Chem. Soc. 1998, 120, 12237-12254.

(Continued)

*Primary Examiner*—Brenda Coleman
(74) *Attorney, Agent, or Firm*—Jennifer S. Sickler; Gardere Wynne Sewell LLP

(57) ABSTRACT

The present invention provides a compound of Formula I, all of its related stereoisomers, and their pharmaceutically acceptable salts, wherein A—B, K, Q, X, Y, Z, R and R1 are as defined in Claim 1. The present invention also provides processes for the preparation thereof, the use thereof in treating immune mediated disease and conditions, and pharmaceutical compositions for use in such therapy

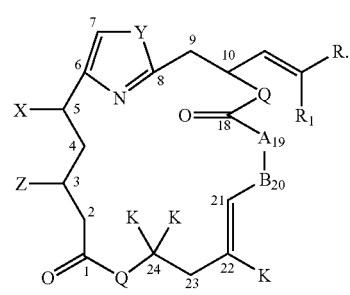

(I)

13 Claims, 4 Drawing Sheets

OTHER PUBLICATIONS

Newman, D., et al., The Influence of Natural Products Upon Drug Discovery, Nat. Prod. Rep., 2000, 17, 215-234.

Hood, K., et al., Induction of Apoptosis by the Marine Sponge (Mycale) Metabolites Mycalamide A and Pateamine, Apoptosis, vol. 6, No. 3, pp. 207-219 (2001).

Cvetkovic, R., et al., ET-743, Drugs 2002: 62 (8): 1185-1192.

Int'l Search Report, Feb. 06, 2004.

Suppl. Partial ESR, Feb. 27, 2006.

G. Pattenden, et al., "The intramolecular Stille reaction in some target natural product syntheses", Journal of Organometallic Chemistry 653, (2002) 261-268, Nottingham, UK.

1: R = H, Pateamine A (Native Pateamine A)
2: R = Boc (BoxPateamine A)

3: Des-mythl, des-amino PatA
   (DMDA PatA)

Scheme 1. a) HOCH$_2$CCl$_3$, SOCl$_2$, benzene, reflux, 5 h, 61%; b) Br$_2$, CCl$_4$, CHCl$_3$, 0 °C, 3h, 36%; c) i) 2,6-lut., CH$_2$Cl$_2$, 25 °C, 12 h ii) TFAA, py., Hünig's base, 0→25 °C, 3 h, 64% (2 steps); d) TBAF, 20 mol% AcOH, THF, -20 °C, 1 h, 96% (10); 25 °C, 12 h, 75% (13); e) PPh$_3$, DIAD, THF, -20 °C, 2 h, 71%; f) 10% Cd/Pb, THF/1M NH$_4$OAc, 25 °C, 2 h, 99%; g) 2,4,6-trichlorobenzoyl chloride, Et$_3$N, DMAP, toluene, THF (0.001 M), 25 °C, 2 h, 92%; h) Pd(CaCO$_3$)/Pb, H$_2$, MeOH, 25 °C, 12 h, 80%; i) 10 mol% [Pd$_2$dba$_3$·CHCl$_3$:AsPPh$_3$=1:8], 17, THF, 25 °C, 2 h, 49%.

Scheme 2. a. PPh$_3$, DIAD, THF, -20 °C, 2h, 71% b. i) HF·py. THF, 25 °C, 24h, 86% ii) Et$_4$NCN, CH$_2$Cl$_2$, 25 °C, 5h, 65% c. Pd(CaCO$_3$)/Pb, H$_2$, MeOH, 12h, 99% d. 10 mol% [Pd$_2$dba$_3$·CHCl$_3$ : AsPPh$_3$ = 1 : 8], THF, 25 °C, 10-18h, 11-76% e. i) 20% TFA, CH$_2$Cl$_2$, 0 °C, 15h, 95% ii) PhCOCl or (CF$_3$CO)$_2$O, DMAP, py., CH$_2$Cl$_2$, 25 °C, 5h, 99%.

Scheme 3. a. Ag$_2$O, MeI, CH$_3$CN, reflux, 9 h, 25%; b. i) TsCl, py., CH$_2$Cl$_2$ 0 °C, 8 h, 65% ii) dimethyl amine (g), THF, -78 °C, 6 h, 85%.

POTENT, SIMPLIFIED DERIVATIVES OF PATEAMINE A

CROSS-REFERENCES TO RELATED APPLICATIONS

The present application claims priority under Title 35, United States Code § 119 of U.S. Provisional Application Ser. No. 60/364,347 filed Mar. 13, 2002.

STATEMENT REGARDING FEDERALLY SPONSORED RESEARCH OR DEVELOPMENT

The present invention was developed with funds from a grant by the National Institute of Health, Grant Number 5R01GM052964-07.

BACKGROUND OF THE INVENTION

1. Field of the Invention

Pateamine A was first isolated from the marine sponge Mycale found off the shores of New Zealand. Northcote, P. T. et al, Tetrahedron Lett., 32:6411–6414 (1991). The natural form bears a thiazole and an E,Z-dienoate within a 19-membered macrocycle and a trienylamine side chain. Two additional pateamines, pateamines B and C, were also isolated. Their structures differ from pateamine A only in the nature of the terminal group of the trienylamine side chain. The structure for all three isolated natural forms is shown below:

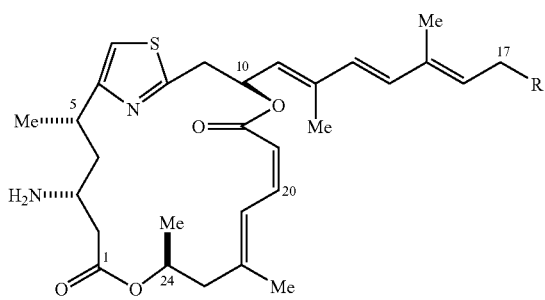

Pateamine A: R = NMe$_2$
B: R = NHMe
C: R = N(O)Me$_2$

Isolated pateamine A ("native pateamine A") is a novel marine product that promises to be quite useful as a biochemical probe and which displays potent imunosuppressive properties with low cytotoxicity. Northcote, P. T.; Blunt, J. W.; Munro, M. H. G. Tetrahedron Lett. 1991, 32, 6411; Alexander Akhiezer, Ph. D. Thesis, Massachusetts Institute of Technology, 1999. In MLR (mixed lyphocyte reaction) assay, IC$_{50}$=2.6 nM while the LCV (lymphocyte viability assay)/MLR ratio is >1000. In comparing native pateamine A to cyclosporin A in a mouse skin graft rejection assay, native pateamine A resulted in a 15 day survival period as opposed to cyclosporin A having only a 10 day survival of the skin graft. Additionally, at high doses, toxicity was at 17% in these studies. For other dose levels, there was no toxicity. All doses were active.

More recently, it was found that native pateamine A specifically inhibits an intracellular step of the T-cell receptor signal transduction pathway leading to IL-2 transcription. Romo, D. et al., J. Am. Chem. Soc., 120:12237–12254 (1998). Two syntheses of native pateamine A have been reported. Rzasa, R. M., et al., J. Am. Chem. Soc., 120: 591–592 (1998), Remuinan, M. J. and Pattenden, G., Tetrahedron Lett., 41:7367–7371 (2000). The utility of these molecules as an immunosuppressant or immunostimulant is severely restricted because the molecule lacks stability. Additionally, natural sources of the molecule are limited. Thus, continuous development of synthetic pateamine derivatives having the same or lower toxicity, potent activity and increased stability is required.

Preliminary studies by a group at PharmMar showed potent activity of native pateamine A in the mixed lymphocyte reaction and also in the mouse skin graft rejection assay. Native pateamine A originally showed activity in a mixed lymphocyte reaction, (IC$_{50}$ 2.6 nM) and in the mouse skin graft rejection assay. Native pateamine A was found to be more potent than cyclosporin A with only low toxicity at high doses but all doses were active. More recent studies, indicate that native pateamine A inhibits a specific intracellular signaling pathway involved in T cell receptor-mediated IL-2 production. Romo, D.; Rzasa, R. M.; Shea, H. A.; Park, K.; Langenhan, J. M.; Sun, L.; Akhiezer, A.; Liu, J. O. J. Am. Chem. Soc. 1998, 120, 12237–12254. In addition to its effect on TCR signaling pathway, native pateamine A has been found to induce apoptosis in certain mammalian cell lines, especially those that are transformed with the oncogene Ras. Hood, K. A.; West, L. M.; Northcote, P. T.; Berridge, M. V.; Miller, J. H. Apoptosis 2001, 6, 207–219.

Analysis of the native pateamine A structure reveals a rigid eastern half (C6–C24) including the thiazole, dienoate, and the triene sidechain, due to extended conjugation, and a more flexible western half (C1–C5). Furthermore, C3-Boc-PatA was found to have only 3–4 fold lower activity than native pateamine A. Id.

2. Description of the Related Art

Natural products have proven to be extremely useful as probes of biological processes. Schreiber, S. L.; Hung, D. T.; Jamison, T. F. Chem. Biol. 1996, 3, 623–639. Examples include the immunosuppressive, microbial secondary metabolites, cyclosporin A, FK506, and rapamycin. Hung, D. T.; Jamison, T. F.; Schreiber, S. L. Chemistry & Biology 1996, 3, 623–639. Marine organisms have also been a rich source of bioactive compounds, which are proving useful as drug leads and biological probes. Newmann, d. J.; Cragg, G. M.; Snader, K. M. Nat. Prod. Rep. 2000, 17, 215–234. For example, bryostatin, epithilone, discodermolide and ecteinascidin show great potential as anti-cancer agents and have revealed novel biological mechanisms of action. Hung, D. T.; Nerenberg, J. B.; Schreiber, S. L. J. Am. Chem. Soc. 1996, 118, 11054–11080; Cvetkovic, R. S.; Figgitt, D. P.; Plosker, G. L. Drugs 2002, 62, 1185–1192.

Marine life has been the source for the discovery of compounds having varied biological activities. The following United States patents have issued for inventions, such as: U.S. Pat. No. 6,057,333, directed to Discorhabdin compounds derived from marine sponges of the genus Batzella or prepared by synthetic methods. These compounds, and pharmaceutical compositions containing them as active ingredients, are useful as immunomodulatory, antitumor agents, and/or caspase inhibitors.

Other patents with compounds from marine organisms include: U.S. Pat. No. 4,548,814, which uses didemnins having antiviral activity that were isolated from a marine tunicate; U.S. Pat. No. 4,729,996, which discloses compounds, having antitumor properties isolated from marine sponges Teichaxnella morchella and Ptilocaulis walpersi; U.S. Pat. No. 4,808,590, which discloses compounds, having antiviral, antitumor, and antifungal properties from the marine sponge Theonella sp.; and U.S. Pat. No. 4,737,510, which discloses compounds having antiviral and antibacterial properties, isolated from the Caribbean sponge *Agelas coniferin*.

Immunomodulators are useful for treating systemic autoimmune diseases, such as lupus erythematosus and diabetes, as well as immunodeficiency diseases. Immunomodulators are also useful for immunotherapy of cancer or to prevent rejections of foreign organs or other tissues in transplants, e.g., kidney, heart, or bone marrow. Examples of immunomodulators include: FK506, muramylic acid dipeptide derivatives, levamisole, niridazole, oxysuran, flagyl, and others from the groups of interferons, interleukins, leukotrienes, corticosteroids, and cyclosporins. Many of these compounds, however, have undesirable side effects and/or high toxicity. New immunomodulator compounds are needed to provide a wider range of immunomodulator function for specific areas with a minimum of undesirable side effects.

Many of the immunomodulators available currently, however, have undesirable side effects and/or high toxicity and are often difficult to synthesize in pharmacologically effective amounts. What is needed is one or more immunomodulative compounds that may be synthetically produced in effective amounts that provide a wider range of immunomodulator function with increased stability and with less undesirable side effects.

BRIEF SUMMARY OF THE INVENTION

The present invention is a compound of Formula I as set out below:

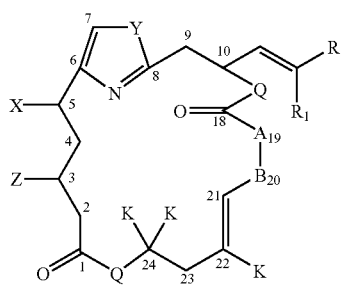

and its pharmaceutically accepted salts, wherein
A—B is ethane, (E) and (Z)-ethene, (E) and (Z)-substituted ethene, ethyne,
K is hydrogen or one-to-three carbon alkyl group,
Q=NH or O,
X is hydrogen, hydroxy, alkoxy, alkyl, aminocarbonyl, amino, alkylamino, dialkylamino, alkoxycarbonylamino,
Y is S, NH, or O,
Z is hydrogen, hydroxy, aminocarbonyl, alkylamino, dialkylamino, alkoxycarbonylammo, but not t-butoxycarbonylamino when $R_4$ is dimethylamino,
$R_1$ is hydrogen or one-to-three carbon alkyl group, and
R is selected from the following:
(a) Alkene of the formula:

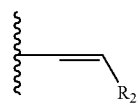

wherein $R_2$ is optionally substituted with one or more substituents selected from alkyl, alkylhydroxy, alkylalkoxy, alkylamino, alkylaminoalkyl, or alkylaminodialkyl;
(b) Alkenylaryl of the formula:

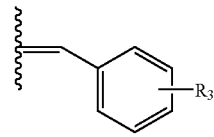

wherein $R_3$ is optionally substituted with one or more substituents selected from hydrogen, alkyl, alkenyl, alkynyl, hydroxy, alkoxy, amino, alkylamino, dialkylamino, trifluoromethane or fluoro; and
(c) Methyldienylpentyl of the formula:

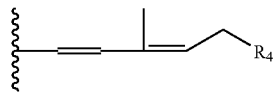

wherein $R_4$ is optionally substituted with one or more substituents selected from hydrogen, alkyl, alkenyl, alkynyl, hydroxy, alkoxy, amino, alkylamino, or dialkylamino; and
(d) Methylalkenylpentyl of the formula:

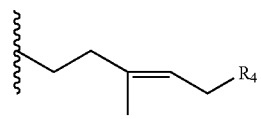

wherein $R_4$ optionally substituted with one or more substituents selected from hydrogen, alkyl, alkenyl, alkynyl, hydroxy, alkoxy, amino, alkylamino, or dialkylamino.

More particularly, the present invention includes a compound with the formula:

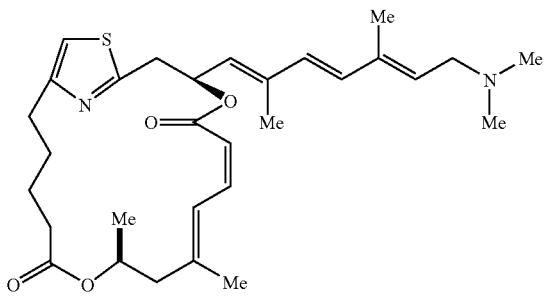

3: Des-methyl, des-amino PatA
(DMDAPatA)

and its pharmaceutically accepted salts.

Yet another embodiment may be a compound having the formula:

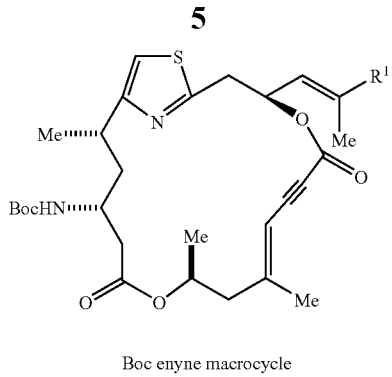

Boc enyne macrocycle and its pharmaceutically accepted salts, wherein R¹ is selected from the following:

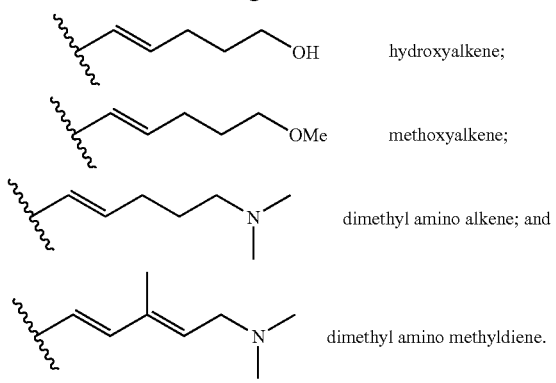

hydroxyalkene;
methoxyalkene;
dimethyl amino alkene; and
dimethyl amino methyldiene.

Another embodiment of the present invention is a compound comprising the formula:

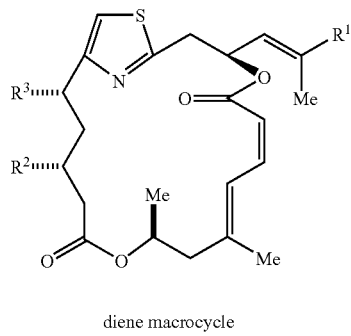

diene macrocycle and its pharmaceutically accepted salts, wherein R¹ is selected from hydroxyalkene, methoxyalkene, dimethyl amino alkene and dimethyl amino methyldiene;

$R^2$ is selected from amino, t-butoxycarbonylamino, hydrogen, phenoxycarbonylamino, and tri-fluromethylacetamide; and $R^3$ is selected from methyl and hydrogen.

Preferred combinations are set out in Table 1 immediately below:

TABLE 1

| $R^1$ | $R^2$ | $R^3$ |
|---|---|---|
| (dimethylamino methyldiene) | $NH_2$ | Me |

TABLE 1-continued

| $R^1$ | $R^2$ | $R^3$ |
|---|---|---|
| (dimethylamino methyldiene) | NHBoc | Me |
| (dimethylamino methyldiene) | H | H |
| (hydroxyalkene) | NHBoc | Me |
| (methoxyalkene) | NHBoc | Me |
| (dimethylamino alkene) | NHBoc | Me |
| (dimethylamino alkene) | NHC(O)OPh | Me |
| (dimethylamino alkene) | NHC(O)CF$_3$ | Me |

Further embodiments of the present invention are the following compounds:

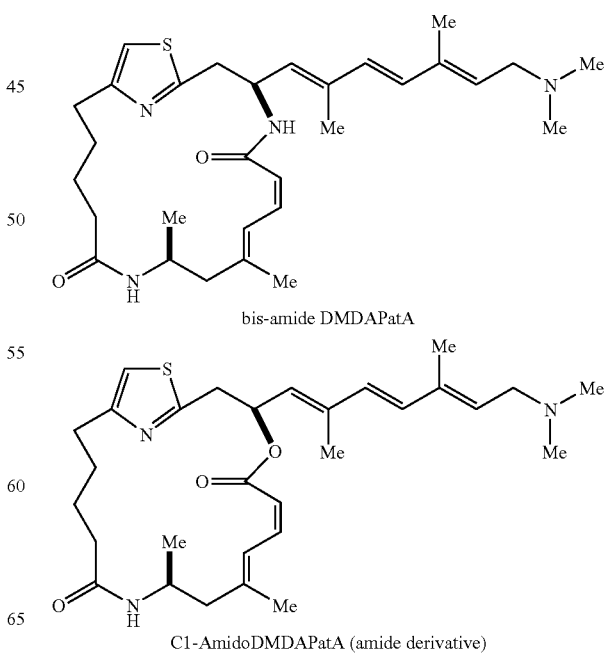

bis-amide DMDAPatA

C1-AmidoDMDAPatA (amide derivative)

-continued

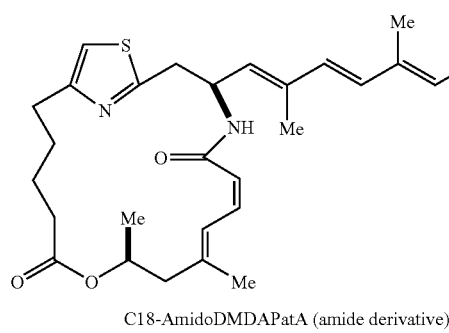

C18-AmidoDMDAPatA (amide derivative)

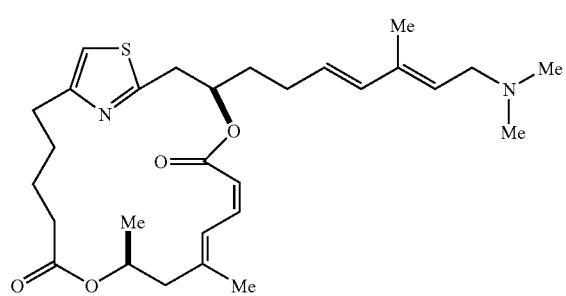

DMDAPatA with unconjugated side chain

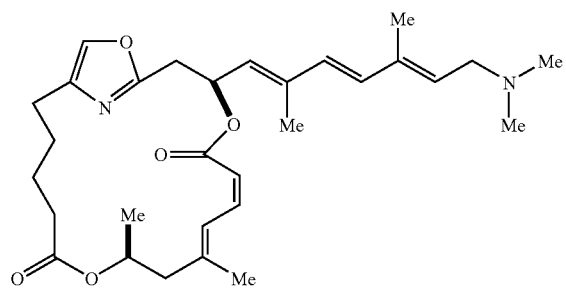

OxoDMDAPatA (oxazole derivative)

-continued

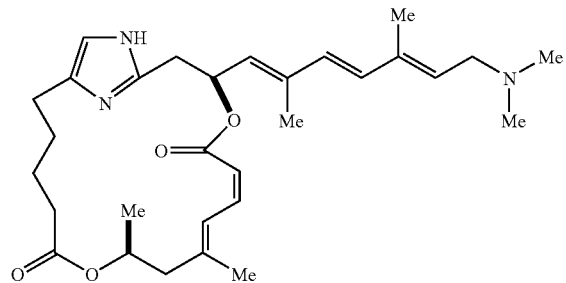

AminoDMDAPatA (imidazole derivative)

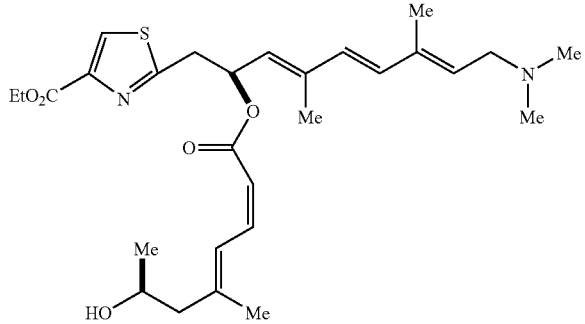

Truncated PatA

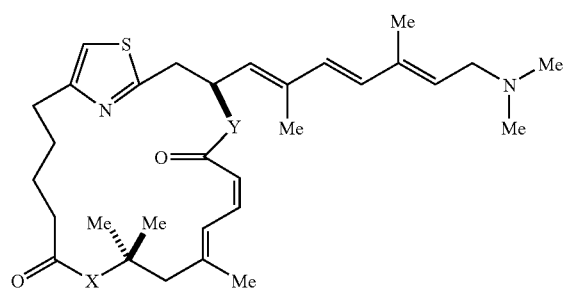

C24-Methyl DMDAPatA (methylated derivative): X, Y = O
C24-Methyl C1-Amido DMDAPatA (methylated derivative):
X = NH or NR, Y = O
C24-Methyl C18-Amido DMDAPatA (methylated derivative):
X = O; Y = NH or NR
C24-Methyl C1, C18-BisAmido DMDAPatA (methylated derivative):
X, Y = NH or NR (where R = alkyl or aryl)

and its pharmaceutically accepted salts.

The present invention also includes a method of making a biotinylated derivative of PatA, comprising the steps of:

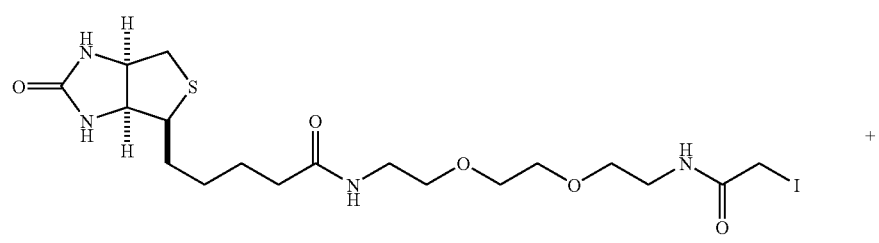

Biotin-PEO-Iodide

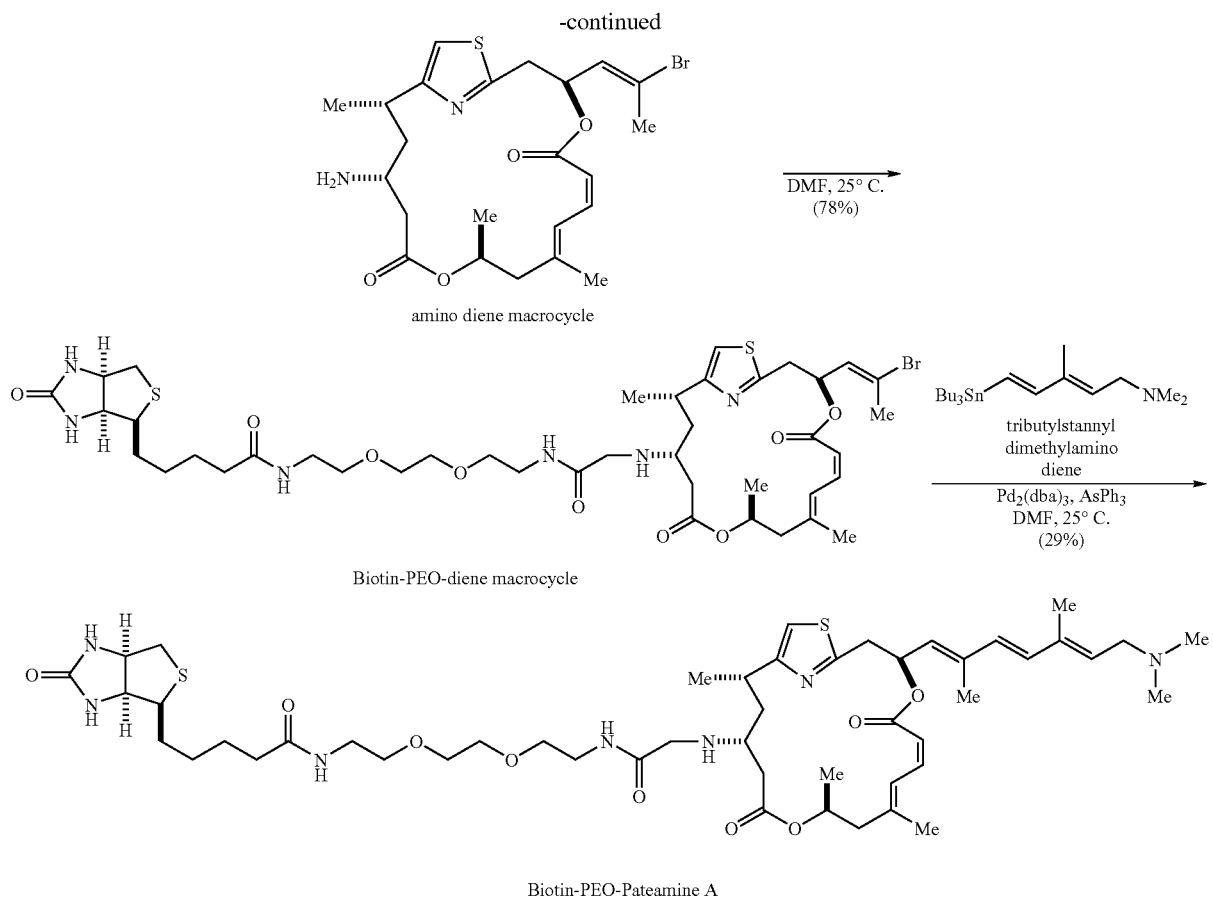

-continued amino diene macrocycle

Biotin-PEO-diene macrocycle

Biotin-PEO-Pateamine A

The present invention includes pharmaceutical compositions and methods of treatment by administering to a person in need thereof the compounds of the present invention. The compounds of the subject invention are useful as an immunoregulator having anti-tumor, anti-fungal or anti-cancer properties. The compounds are also useful in graft versus host rejection therapy, autoimmune diseases, chemotherapy and/or treatment of infectious diseases. The compounds of the present invention overcome the limitation of the native molecule (as produced in nature), having potent activity and increased stability with the same or lower toxicity.

Pateamine A ("native pateamine A"), a marine metabolite from *Mycale* sp., is a potent inhibitor of the intracellular signal transduction pathway emanating from the T-cell receptor leading to the transcription of cytokines such as interleukin (IL-2). Based on the structure of native pateamine A, initial biological results, and molecular modeling studies, the presence of distinct binding and scaffolding domains in the native pateamine A structure with respect to interactions with its putative cellular receptor(s) has been shown. A simplified PatA derivative (desmethyl, desamino PatA, DMDA PatA, 3 as shown in FIG. 1) was prepared by employing a convergent Hantzsch coupling strategy via total synthesis of the molecule. This derivative was prepared in 10 fewer synthetic steps relative to native pateamine A and was found to exhibit equal to greater potency ($IC_{50}$ 0.81±0.27 nM) in inhibition of IL-2 production relative to native pateamine A ($IC_{50}$ 4.01±0.94 nM). In addition, as a means to find more stable derivatives and gain further insights into structure-activity relationships, PatA derivatives have been synthesized and studied in the IL-2 reporter gene assay. Many of these derivatives displayed lower potency but marked stability relative to the natural product and provide further insights into the nature of the binding domain required for activity.

A hypothesis was developed regarding a potential binding and scaffolding domain in the immunosuppressive marine natural product, pateamine A ("native pateamine A"). Premised on preliminary biological and molecular modeling studies, an analysis of the native pateamine A structure was prepared. A simplified derivative, DMDA PatA, devoid of the C3-amino and C5-methyl groups was found to have greater potency than native pateamine A in the IL-2 reporter gene assay. As evidenced in the analysis, the sector of the molecule (C1–C5) serves as a scaffold for the remaining conformationally rigid sectors (C6–C24) of the molecule including the thiazole, the dienoate, and the triene sidechain. This result is reminiscent of similar receptor binding proposals put forth in early studies of other cyclic peptide and macrocyclic immunosuppressive natural products, namely cyclosporin A, FK506, and rapamycin. Hung, D. T.; Jamison, T. F.; Schreiber, S. L. Chemistry & Biology 1996, 3, 623–639. However, in those cases, the domains were renamed effector and binding domains because these natural products were found to bind two cellular proteins acting as a molecular "glue."

Importantly, the synthesis of this derivative (14 versus 24 steps from crotyl alcohol; longest linear sequence) is greatly simplified relative to PatA (1 as shown in FIG. 1), native pateamine A. As previously observed, C3-amino acylated derivatives retain activity in the IL-2 reporter gene assay. In addition, a subtle interplay between the dienoate sector (C18–C22) and the triene sidechain was revealed when dienoate versus enynoate-containg macrocycles were compared. The importance of macrocycle conformation and sidechain functionality in binding of native pateamine A to its putative cellular receptor is evidenced.

BRIEF DESCRIPTION OF THE SEVERAL VIEWS OF THE DRAWINGS

For better understanding of the invention and to show by way of example how the invention may be carried into effect, reference is now made to the detail description of the invention along with the accompanying figures in which corresponding numerals in the different figures refer to corresponding parts and in which.

DETAILED DESCRIPTION OF THE INVENTION

Figure 1:
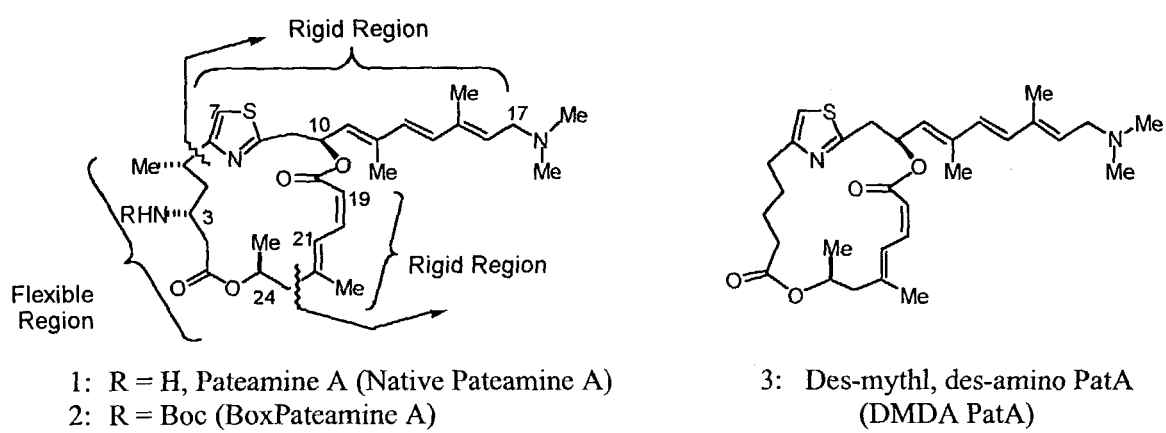
FIG. 1 shows the chemical structure of native pateamineA, boc pateamine A and novel demda PatA.

The present invention is a compound of Formula I as set out below.

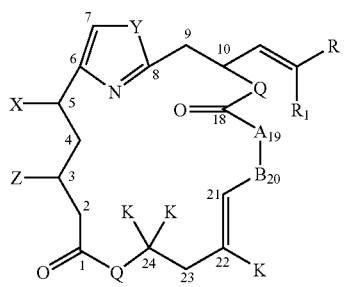

and its pharmaceutically accepted salts, wherein
A—B is ethane, (E) and (Z)-ethene, (E) and (Z)-substituted ethene, ethyne,
K is hydrogen or C1–C3 alkyl,
Q=NH or O,
X is hydrogen, hydroxy, alkoxy, alkyl, aminocarbonyl, amino, alkylamino, dialkylamino, alkoxycarbonylamino,
Y is S, NH, or O,
Z is hydrogen, hydroxy, aminocarbonyl, alkylamino, dialkylamino, alkoxycarbonylamino, but not t-butoxycarbonylamino when $R_4$ is dimethylamino,
$R_1$ is hydrogen or $C_1$–$C_3$ alkyl, and
R is selected from the following:
 (a) Alkene of the formula:

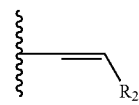

wherein R2 is optionally substituted with one or more substituents selected from alkyl, alkylhydroxy, alkylalkoxy, alkylamino, alkylaminoalkyl, or alkylaminodialkyl;
 (b) Alkenylaryl of the formula:

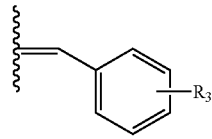

wherein $R_3$ is optionally substituted with one or more substituents selected from hydrogen, alkyl, alkenyl, ankynyl, hydroxy, alkoxy, amino, alkylamino, dialkylamino, trifluromethane, or fluoro; and
 (c) Methyldienylpentyl of the formula:

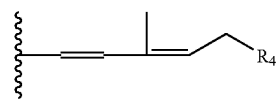

wherein $R_4$ is optionally substituted with one or more substituents selected from hydrogen, alkyl, alkenyl, alkynyl, hydroxy, alkoxy, amino, alkylamino, or dialkylamino; and
 (d) Methylalkenylpentyl of the formula:

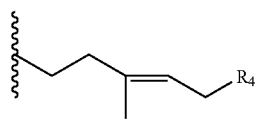

wherein $R_4$ is optionally substituted with one or more substituents selected from hydrogen, alkyl, alkenyl, alkynyl, hydroxy, alkoxy, amino, alkylamino, or dialkylamino.

Native pateamine A consists of separate binding (C6–C24) and scaffolding (C1–C5) domains. Molecular modeling studies and the total synthesis and biological analysis of a simplified derivative, devoid of the C3-amino and C5-methyl groups (DMDA PatA) is provided. The synthesis of DMDA PatA incorporates a convergency-building strategy involving a Hantzsch thiazlole coupling. In addition, the synthesis and biological testing of other pateamine A derivatives are provided having the stability in comparison to the native pateamine A structure. In particular, stabilization of the acid sensitive triallylic acetate moiety (i.e. C10 position) is provided in such derivatives.

Molecular Modeling Studies of Native Pateamine A and DMDA PatA

The presence of binding and scaffolding domains in native pateamine A were verified using molecular mechanics/dynamics (MM/MD) calculations. Simulated annealing was used to determine the conformational space of native pateamine A. An overlay of the 100 structures obtained from the simulated annealing, in which the C11–C16 segment of the triene moiety is overlaid, shows a "mushroom" structure. From the 100 structures, 13 unique conformers (Table 1) were identified within 3 kcal/mol of the lowest energy conformer. Extensive NMR studies of native pateamine A by the Munro and Blunt groups revealed a key cross-ring nOe in $CDCl_3$ between $H_{C3}$ and $H_{C21}$ (see FIG. 1 for numbering scheme), indicating that these two hydrogen atoms should be less than approximately 3 Å of one another. Robert, G. C. K., Ed.; Osford Univ. Press, 1993, Ch. 10. The MM/MD calculations gave conformers that had $H_{C3}-H_{C21}$ distances ranging from 3.2 to 7.1 Å, and a distance of 4.3 Å for the lowest energy conformation.

To obtain better energetics and refined structures, the 13 unique conformations determined at the MM/MD level of theory, were optimized at the DFT level of theory using the B3LYP functional. Frequency calculations were performed to obtain free energies and ensure that each structure had zero imaginary frequencies. Table 2 lists the CVFF relative energies ($\Delta E(0K)$) and $H_{C3}-H_{C21}$ bond distances, and B3LYP relative free energies ($\Delta G^0$) and $H_{C3}-H_{C21}$ bond distances for the 13 unique conformers.

TABLE 2

Energetics (kcal/mol) and $H_{C3}-H_{C21}$ bond distances (Å) for the 12 unique PatA (DMDA PatA) conformers at the CVFF and B3LYP levels of theory.

| Conformer | CVFF $\Delta E$ (0K) (kcal/mol) | $H_{C3}-H_{C21}$ Distance (Å) | B3LYP[a] $\Delta G^\circ$ (kcal/mol) | $H_{C3}-H_{C21}$ Distance (Å) |
|---|---|---|---|---|
| A | 0.0 | 4.34 | 9.0 (7.9) | 4.96 (4.83) |
| B | 0.3 | 4.24 | 8.1 | 4.92 |
| C | 0.4 | 3.23 | 4.8 | 3.28 |
| D | 0.8 | 6.09 | 10.1 | 6.10 |
| E | 1.3 | 3.94 | 0.0 (0.0) | 4.52 (4.37) |
| F | 1.4 | 6.17 | 13.0 | 5.99 |
| G | 1.4 | 3.24 | 3.3 (2.3) | 3.30 (3.26) |
| H | 2.0 | 3.78 | 3.3 | 3.57 |
| I | 2.0 | 3.75 | 9.3 | 3.37 |
| J | 2.1 | 3.22 | 7.5 | 3.50 |
| K | 2.5 | 3.78 | 8.2 | 3.43 |
| L | 2.8 | 5.72 | 4.6 | 5.81 |
| M | 2.8 | 3.79 | 3.2 | 3.54 |

[a]Values in parenthesis are for the corresponding DMDA PatA conformer.

In Table 2, the following abbreviations are used: CVFF is Consistent Valence Force Field, DFT is Density Functional Theory, and B3LYP is is Becke three parameter hybrid exchange functional and the Lee-Yang-Parr correlation functional.

A large discrepancy between the CVFF and B3LYP energies with an underestimation of the difference in conformational energy by CVFF is evident. While CVFF energies were quite different from B3LYP, the structures were similar. An overlay of the 13 B3LYP optimized conformations was made. Inspection of the overlay revealed two basic conformations: 1) lower energy extended structures, leaving the majority of the triene moiety exposed and 2) higher energy conformations having the macrocycle folded over the triene moiety. DFT is known to underestimate van der Waal interactions; therefore, the $H_{C3}-H_{C21}$ distance appeared to be underestimated.

The lowest energy conformer identified at the B3LYP level, $H_{C3}-H_{C21}$, has a distance of 4.5 Å, longer than anticipated in light of the cross-ring nOe. Another conformer has only 3.3 kal/mol higher in energy than the lowest energy conformer having an $H_{C3}-H_{C21}$ distance of 3.3 Å, in much better agreement with the cross-ring nOe.

Of the 13 conformations studied, four have an $H_{C3}-H_{C21}$, distance less than 4 Å, and within 5 kcal/mol of the lowest energy conformer. An overlay of the conformations are within 5 kcal/mol of the lowest energy conformer and have an $H_{C3}-H_{C21}$, distance consistent with the NMR data. As shown in FIG. 1, the extended conformations differ primarily in the C1–C5 region, indicating a flexible region, while the thiazole, triene, and dienoate regions (C6–C22) are relatively rigid in nature. The thiazole has two conformations that are approximately 180 degrees from each other i.e. simultaneous rotation around C5–C6 and C8–C9. Therefore, the relative position of the plane containing the thiazole ring atoms in these conformations changes very little, but the nitrogen and sulfur atoms exchange positions.

Simulated annealing was also used to investigate the conformational space of DMDA PatA. An overlay of the 100 structures obtained from the simulated annealing, in which the C11–C16 segment of the triene moiety is overlaid, shows a "mushroom" structure similar to that found for native pateamine A. Due to the computational cost of the B3LYP calculations and the similar results obtained from the CVFF calculations, only three conformations (A, E, and G) were optimized at the B3LYP level of theory for DMDA PatA. The relative free energies for DMDA PatA are similar to those found for native pateamine A (Table 2) with the difference in free energy between conformations being about 1 kcal/mol less than that for native pateamine A. An overlay of the lowest energy conformer of native pateamine A and the corresponding DMDA PatA conformer was used. In addition, an overlay of the lowest energy conformer that also satisfies the nOe constraint for native pateamine A and the corresponding DMDA PatA conformer was used. As can be seen by this analysis, native pateamine A and DMDA PatA have similar structures and energetics using similar minimization parameters.

These structural studies, in combination with the previously reported potent biological activity of acylated C3-amine derivatives (e.g. 2, R=Boc), suggested the presence of possible separate binding (C6–C24) and scaffolding (C1–C5) domains in the native pateamine A structure. Romo, D.; Rzasa, R. M.; Shea, H. A.; Park, K.; Langenhan, J. M.; Sun, L.; Akhiezer, A.; Liu, J. O. J. Am. Chem. Soc. 1998, 120, 12237–12254. Many protein ligands are known to change conformations on binding to their receptors or alternatively, the binding event leads to a more defined conformation. Rosen, M. K.; Belshaw, P. J.; Alberg, D. G.; Schreiber, S. L. Bio. Med. Chem. Lett. 1992, 2, 747–753. The preliminary biological data and the modeling described above, allows synthesis of a simplified PatA derivatives including DMDA PatA that are devoid of the C3-amino and C5-methyl groups.

Synthesis of PatA Derivatives

Figure 2:
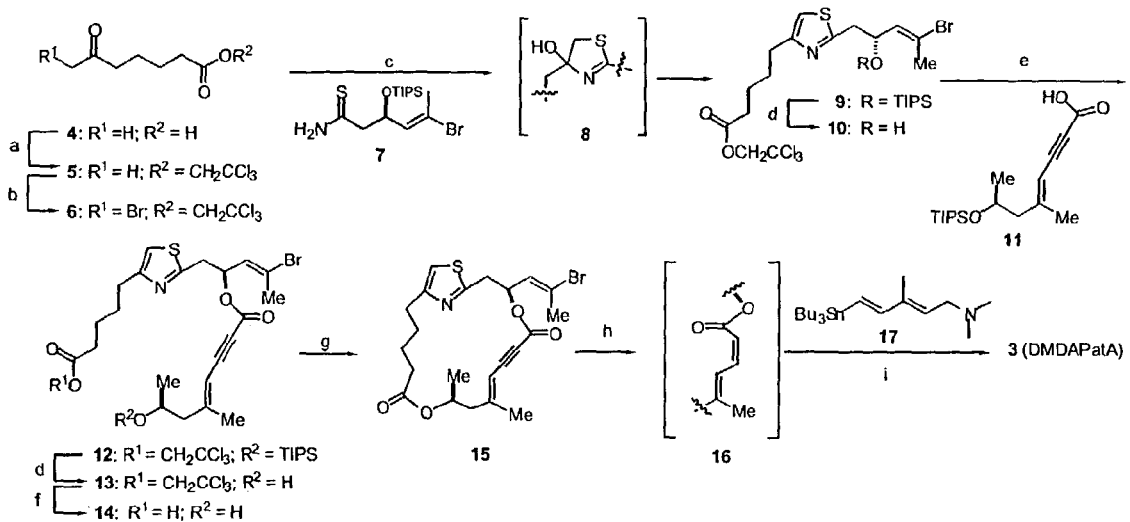
FIG. 2 depicts the synthesis of DMDA PatA using Scheme 1.

For the synthesis of DMDA PatA 3, a more convergent strategy to the C1–12 thiazole-containing fragment employing a Hantzsch coupling reaction (FIG. 2, Scheme 1). Pattenden made use of a related-strategy in the synthesis of native pateamine A. Remuinan, M. J.; Pattenden, G. Tetrahedron Lett. 2000, 41, 7367–7371. As shown in FIG. 2, the synthesis of the requisite bromoketone 6 commenced with esterification and bromination of 6-oxoheptanoic acid (4). Hantzsch thiazole coupling between this bromoketone and the previously described thioamide 7 using modified Meyers' conditions provided thiazole 9 in good overall yield (64%). Romo, D.; Rzasa, R. M.; Shea, H. A.; Park, K.; Langenhan, J. M.; Sun, L.; Akhiezer, A.; Liu, J. O. J. Am. Chem. Soc. 1998, 120, 12237–12254; Aguilar, E.; Meyers, A. I. Tetrahedron Lett. 1994, 35, 2473–2476. A critical prerequisite for optimal yields in this coupling was purification of the intermediate thiazoline 8 prior to the dehydration step in contrast to our previous applications of this reaction, in which this process could be performed in a single pot. Romo, D.; Rzasa, R. M.; Shea, H. A.; Park, K.; Langenhan, J. M.; Sun, L.; Akhiezer, A.; Liu, J. O. J. Am. Chem. Soc. 1998, 120, 12237–12254. Deprotection of the TIPS ether followed by a Mitsunobu coupling with the TIPS protected version of the previously described enyne acid 11 gave the macrocyclic precursor 12. Id. Deprotection of the TIPS ether and trichloroethyl ester of diester 12 followed by Yamaguchi macrocyclization gave macrocycle 15. Dong, Q.; Anderson, C. E.; Ciufolini, M. A. Tetrahedron Lett. 1995, 36, 5681–5682; Inanaga, J.; Hirata, K.; Saeki, H.; Katsuki, T.; Yamaguchi, M. Chem. Soc. Japan 1979, 52, 1989–1993. Subsequent Lindlar reduction gave E,Z-diene 16 and Stille coupling with the previously described dienyl stannane 17 gave DM DAPatA (3) in 11 steps from thioamide 7. Id., see also, Farina, V.; Krishnan, B. J. Am. Chem. Soc. 1991, 113, 9585–9595.

Figure 3:
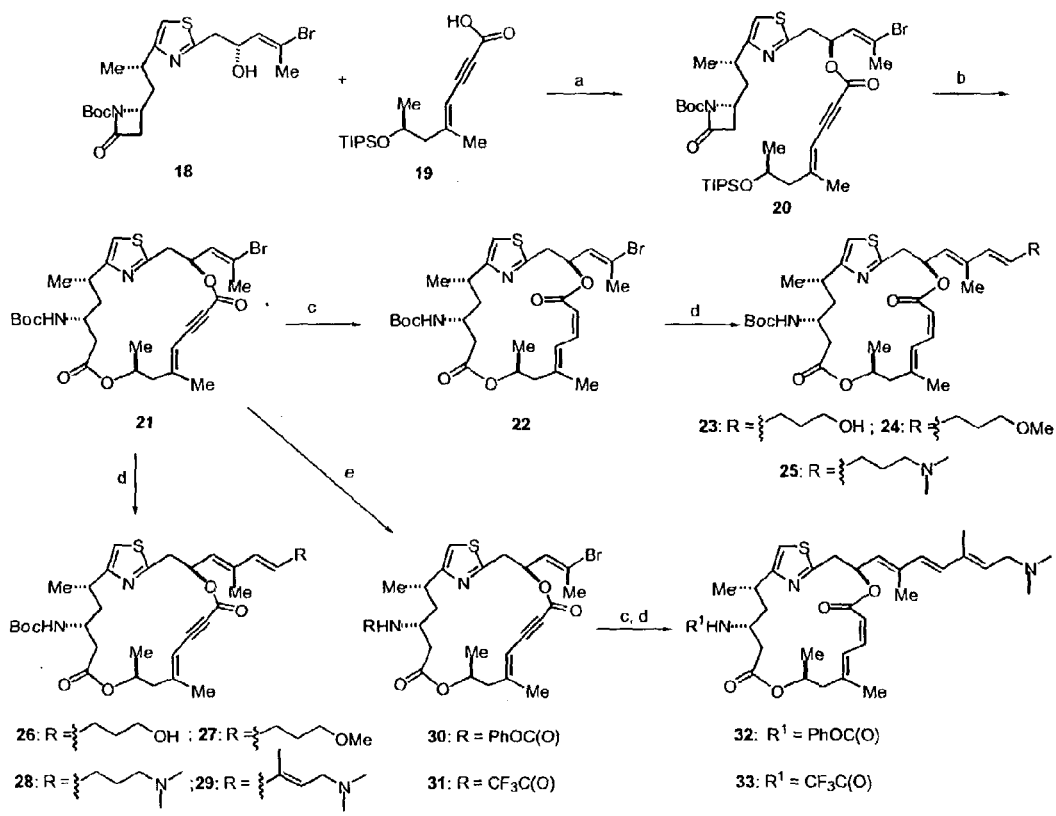
FIG. 3 shows the synthesis of additional PatA derivatives using Scheme 2.

The synthesis of additional PatA derivatives with only minor structural variations began with the previously described β-lactam 18 (FIG. 3, Scheme 2). The synthesis of all derivatives in this series mirrored that previously reported for the total synthesis of native pateamine A. Romo, D.; Rzasa, R. M.; Shea, H. A.; Park, K.; Langenhan, J. M.; Sun, L.; Akhiezer, A.; Liu, J. O. J. Am. Chem. Soc. 1998, 120, 12237–12254. Introduction of side chain via a Stille coupling reaction as the final step in the synthesis is preferred partly to the polarity introduced by the tertiary amine, but primarily due to the instability associated with the triallylic ester moiety.

Figure 4:
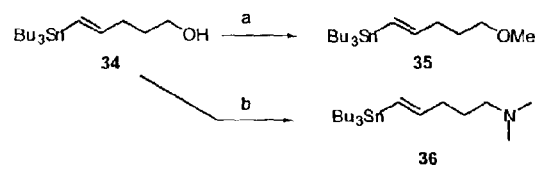
FIG. 4 shows the required stannanes for side chain-modified PatA derivatives using Scheme 3.

Derivatives 23–25 and 26–28 were prepared to determine the structural flexibility tolerated on the sidechain of PatA and also to improve stability of the acid labile triallylic acetate moiety by removal of one unsaturation. For this purpose, the required stannanes for sidechain-modified PatA derivatives were prepared by standard conditions and stannylcupration was performed as described previously for vinyl stannane 17 (FIG. 4, Scheme 3). Romo, D.; Rzasa, R. M.; Shea, H. A.; Park, K.; Langenhan, J. M.; Sun, L.; Akhiezer, A.; Liu, J. O. J. Am. Chem. Soc. 1998, 120, 12237–12254. The C3-Boc protecting group had previously been found to have a minor effect on activity (2–3 fold decrease in activity), therefore for ease of handling, this group was retained in all derivatives. PatA derivatives bearing a dienyl alcohol (23 and 26) and a dienyl methyl ether (26 and 27) were synthesized. In addition, derivative 25 bearing the identical side-chain found in PatA with the exception of one unsaturation and the C16 methyl group was prepared. The effect of a more rigid macrocycle (i.e. enyne vs dienoate) on biological activity was investigated by synthesis of enynes 26–29. These derivatives were readily prepared by omission of the Lindlar reduction step (FIG. 3, Scheme 2).

Due to the aforementioned activity of C3-Boc PatA, two additional C3-amino derivatives were prepared with the expectation that they should have similar potency. In this regard, the C3-phenyl carbamate 32 and the C3-trifluoroacetamide 33 were synthesized by deprotection of Boc-macrocycle 21 followed by acylation to give macrocycles 30 and 31. Subsequent Lindlar reduction and Stille reaction gave the C3-acylated derivatives 32 and 33.

The ability of these derivatives to inhibit T cell receptor-mediated IL-2 production was analyzed using an IL-2 reporter gene assay. In this assay, a plasmid encoding a reporter gene (luciferase) under the control of the IL-2 promoter was first introduced into Jurkat T cells by transfection. The transfected Jurkat T cells are then stimulated with two pharmacological agents, phorbol myristyl acetate (PMA), which activates protein kinase C, and inonmycin, which allows calcium ion to enter T cells to activate calmodulin and calcineurin. Together, PMA and ionomycin recapitulate T cell receptor signaling, leading to the activation of the luciferase reporter gene by activating the IL-2 promoter. The ability of PatA and its analogs to block T cell receptor-mediated IL-2 expression was measured by their effects on this reporter gene assay. Su, B.; Jacinto, E.; Hibi, M.; Kallunki, T.; Karin, M.; Ben-Neriah, Y. Cell 1994, 77, 727–736.

Most derivatives were in general less potent than native pateamine A, PatA (1). As expected, the C3-phenyl carbamate derivative 32 was found to have comparable activity (~15 nM) to BocPatA (2, 16–17 nM). However, the reduced activity of the trifluoroacetamide 33 (~303 nM) may be due to the increased polarity of this substituent leading to poorer cell permeability. However, a possible trend was observed upon comparison of dienoate macrocyclic (23–25) versus enynoate macrocyclic (26–29) derivatives. Enyne derivatives having an a more rigid macrocycle than the natural product and bearing oxygen rather than nitrogen at the terminus of the side chain (i.e. 26 and 27) were found to have activities in the IL-2 reporter gene assay ranging from 55–335 nM. However, enyne derivatives (i.e. 28 and 29) with side chains more closely resembling the natural product (i.e. amino end groups) had no activity. Futhermore, the dienoate derivatives (i.e. 23 and 24) having macrocycle conformations similar to the natural product but bearing oxygen rather than nitrogen at the terminus of the side chain had very low activity. However, once nitrogen is introduced into the sidechain, as in derivative 25, activity is restored (328 nM). Thus, it would appear that an oxygenated sidechain compensates for the change in macrocycle conformation that occurs upon introduction of an enyne. However, oxygen rather than nitrogen on the side chain leads to low activity when coupled to the natural dienoate-containing macrocycle. It is imaginable that changes in the conformation of the macrocycle results in a reorientation of the sidechain that cannot be accommodated by the protein receptor. However, replacement of a charged tertiary amino group with a neutral and smaller hydroxyl or methoxy groups allows for the binding of the derivative with these two structural alterations.

The derivative providing direct support for the binding/scaffolding hypothesis is DMDA PatA 3. This derivative displayed similar to greater potency ($IC_{50}$ 0.8±0.3 nM) relative to natural pateamine PatA ($IC_{50}$ 4.0±0.9 nM) in its ability to inhibit expression of the IL-2 reporter gene in stimulated Jurkat T cells. The hypothesis that the C1–C5 segment of native pateamine A does not interact directly with its putative cellular receptor but may serve as a scaffold to define and maintain the macrocyclic conformation is supported in accordance with the results above. Importantly, DMDA PatA 3 is more stable than native pateamine A (stable in $CDCl_3$ for 3–4 weeks at 25° C.). Native pateamine A decomposes in $CDCl_3$ at 25° C. in <10 minutes.

TABLE 3

IL-2 reporter gene assay (transfected Jurkat cells) activity of pateamine A and derivatives.

| cmpd. | R¹ | IC$_{50}$ (nM) | cmpd. | R¹ | R² | R³ | IC$_{50}$ (mM) |
|---|---|---|---|---|---|---|---|
| 26 | ⋰⋰⋰ OH | 335 ± 183 | PatA (1) | ⋰⋰⋰ N(Me)₂ | NH₂ | Me | 4.01 ± 0.938 |
| 27 | ⋰⋰⋰ OMe | 55.1 ± 15.5 | 3 | ⋰⋰⋰ N(Me)₂ | H | H | 0.808 ± 0.274 |
| 28 | ⋰⋰⋰ N(Me)₂ | NA[a] | 23 | ⋰⋰⋰ OH | NHBoc | Me | >1000[b] |
| 29 | ⋰⋰⋰ N(Me)₂ | NA[a] | 24 | ⋰⋰⋰ OMe | NHBoc | Me | >1000[b] |
| | | | 25 | ⋰⋰⋰ N(Me)₂ | NHBoc | Me | 328 ± 119 |
| | | | 32 | ⋰⋰⋰ N(Me)₂ | NHC(O)OPh | Me | 15.4 ± 6.05 |
| | | | 33 | ⋰⋰⋰ N(Me)₂ | NHC(O)CF₃ | Me | 303 ± 93.2 |

[a]Not active.
[b]Inhibition activity was observed, but it did not reach 50% even with the highest concentration tested.
[c]It should be noted that the IC$_{50}$ value for PatA in this particular assay is ten fold higher than that previously reported. It seems that Jurkat cells appear to vary in their sensitivity to PatA, depending in part on the number of passages they have undergone. All IC$_{50}$ values listed in this table were determined using the same population of Jurkat T cells.

The present invention also encompasses pharmaceutically acceptable salts of Formula I where they can be formed. Pharmaceutically acceptable salts may be formed from Formula B compounds and a pharmaceutically acceptable organic or inorganic acid including, but not limited to hydrochloric acid, sulfuric acid, phosphoric acid, acetic acid, maleic acid, fumaric acid, toluenesulfonic acid, benzoic acid, succinic acid and the like. Such salts may be formed during or after the synthesis of the compound of Formula I.

In general, a pharmaceutically acceptable salt of the present invention may be administered in a pharmaceutically acceptable carrier to an animal or a human. In order to obtain systemic immune suppression, injection of the compound in a liquid carrier such as saline may prove suitable. For local effects, topical administration in an ointment or cream may have better function. All carriers should be chosen so as not to counteract the desired effects of the compound (immunosuppression or immunostimulation). Additionally, carriers should be chosen to promote the stability of the compound. In both in vitro and in vivo applications, more than one compound of Formula I may be combined with another compound of Formula I or a different compound all together to achieve multiple effects or a synergistic effect.

Immunosuppressive compounds of Formula I may be used to prevent long-term or short-term transplant rejection. Immunostimulant compounds may be used to counter autoimmune diseases, provide chemotherapy or other cancer treatments and to fight infections, including fungal infections.

The active compounds disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

EXAMPLES

Example 1

Synthesis of Biotin-PEO-macrocycle

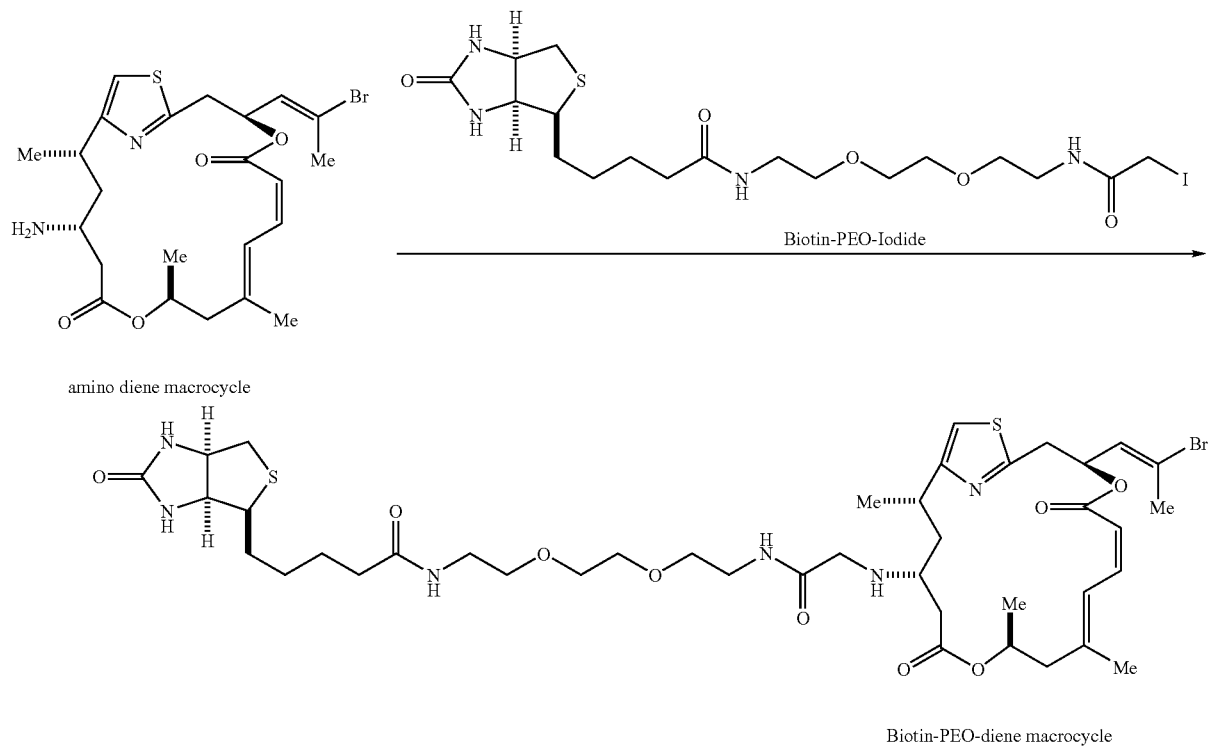

To a stirred solution of amino diene macrocycle (6 mg, 0.0117 mmol) in DMF were added biotin-PEO-iodide (6.3 mg, 0.017 mmol) and K$_2$CO$_3$ (3.2 mg, 0.0234 mmol). After 15 h, an additional amount of biotin-PEO-iodide (6.3 mg, 0.0117 mmol) was added. The resulting solution was stirred at 25° C. for 16 h and concentrated in vacuo. Purification of the residue by directly loading on a flash column containing SiO$_2$ and eluting with EtOAc:n-Hex.:Et$_3$N (45:52:8) to CHCl$_3$:MeOH (9:1) gave 8.5 mg (78%) of biotin-PEO-diene macrocycle as a pale yellowish oil: $^1$H-NMR (500 MHz, CDCl$_3$) δ7.69 (t, J=6 Hz, 1H), 7.01 (d, J=7.2 Hz, 1H), 6.77 (s, 1H), 6.72 (dd, J=6.6, 7.2 Hz, 1H), 6.52 (br s, 1H), 6.01 (dt, J=2, 9.5 Hz), 5.94 (d, j=9.5 Hz, 1H), 5.79 (br s, 2H), 5.42 (d, J=6.6 Hz, 1H), 5.12 (br s, 1H), 5.08–5.04 (m, 1H), 4.51–4.48(m, 1H), 4.33–4.30 (m, 1H), 3.61–2.84 (m, 15H), 2.45 (s, 3H), 2.33–1.21 (m, 18H), 1.99 (s, 5H), 1.80 (s, 3H); MS (ESI) m/z 927 [M+H]$^+$.

Example 2

Biotin-PEO-Pateamine A

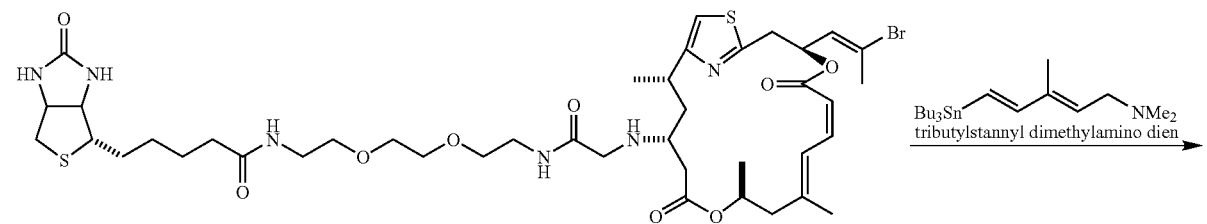

-continued

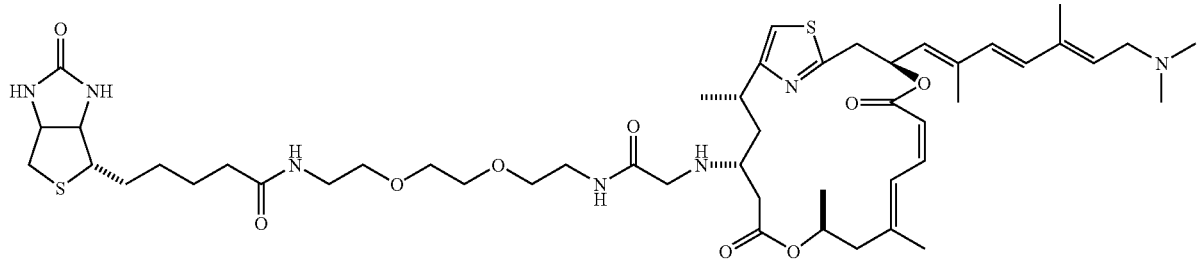

Biotin-PEO-Pateamine A

To a flask charged with $Pd_2dba_3 \cdot CHCl_3$ (1.7 mg, 0.0016 mmol) and triphenyl arsine (4.1 mg, 0.013 mmol) was added 0.1 mL of degassed THF (by several freeze/thaw cycles). The final concentration of this palladium catalyst stock solution was 0.031 M. To a solution of Biotin-PEO-diene macrocycle (7 mg, 0.0075 mmol) and tributylstannyl dimethyl amino diene (9.3 mg, 0.0225 mmol) in 0.1 ml of THF was added 0.024 mL of palladium catalyst. The resulting solution was stirred at 25° C. for 14 h. and concentrated in vacuo. Purification of the residue by directly loading on a C18 reverse phase chromatography eluting with $H_2O$:$CH_3CN$:AcOH:$Et_3N$ (65:35:3 mmol:1.5 mmol) gave 2.1 mg of biotin-PEO-pateamine A as a pale yellowish oil. The residue was loaded on an amino cartridge pre-equilibrated with MeOH and eluted with MeOH to give 2.1 mg (29%) of biotin-PEO-pateamine A as a pale yellowish oil: $^1$H-NMR (500 MHz, benzene-d6) δ7.78 (br t, 1H), 6.67–6.60 (m, 1H), 6.53 (s, 1H), 6.51 (dd, J=12, 6.5 Hz, 1H), 6.37 (br s, 1H), 6.28 (d, J=16 Hz, 1H), 6.18 (d, J=16 Hz, 1H), 5.66 (br t, 1H), 5.61 (d, J=12 Hz, 1H), 5.46 (d, J=9 Hz, 1H), 5.04–4.98 (m, 1H), 4.80 (br s, 1H), 3.06–2.07 (m, 22H), 2.07 (s, 6H), 1.93–0.78 (m, 12 H), 1.84 (s, 3H), 1.75 (s, 3H), 1.66 (s, 3H), 1.51 (s, 3H), 1.31 (d, J=6.5 Hz, 3H), 1.01 (d, J=6.5 Hz, 3H); HRMS (ESI) Calcd for $C_{49}H_{75}N_7O_9S_2$ [M+H]: 970.5145 found: 970.5135

Example 3

Molecular Modeling Details

Molecular mechanics and dynamics calculations were performed using the OFF (Open Force Field) program with CVFF 950 (Consistent Valence Force Field) as implemented in Cerius 4.6 (Accelrys, Inc., San Diego, Calif.). Simulated annealing was carried out for 280.0 ps, over a temperature range of 300–500 K, using the Nosé temperature thermostat, a relaxation time of 0.1 ps, and a time step of 0.001 ps. After each annealing step, the structure was minimized, leading to 100 minimized structures. A dielectric constant of 86.75 was used to simulate bulk solvation in water. A rigid body least squares fit algorithm (as implemented in Cerius 4.6) was used to overlay the 100 structures obtained from the simulated annealing and the 16 B3LYP optimized structures. The carbons belonging to the triene region were the only atoms used in the least squares fit. After all molecules were overlayed, a visual inspection of the 24 structures within 3 kcal/mol of the lowest energy structure was used to extract 13 unique conformations of the flexible ring portion of the molecule. Full geometry optimizations (gas phase) and frequency calculations were performed for the 13 unique conformations using Density Functional Theory (DFT) with the Becke three parameter hybrid exchange functional and the Lee-Yang-Parr correlation functional (B3LYP) as implemented in the Gaussian 98 suite of programs. Parr, R. G.; Yang, W. Density-functional theory of atoms and molecules Oxford University Press, Oxford, 1989; Becke, A. D.; Phys. Rev. A. 1988, 38, 3098; Becke, A. D. J. Chem. Phys. 1993, 98, 1372; Becke, A. D. J. Chem. Phys. 1993, 98, 5648; Lee, C.; Yang, W.; Parr, R. G. Physical Review B 1988, 37, 785; Gaussian 98 (Rev. A.9), Frisch, M. J.; Trucks, G. W.; Schlegel, H. B.; Scuseria, G. E.; Robb, M. A.; Cheeseman, J. R.; Zakrzewski, V. G.; Montgomery, J. A.; Stratmann, R. E.; Burant, J. C.; Dapprich, S.; Millam, J. M.; Daniels, A. D.; Kudin, K. N.; Strain, M. C.; Farkas, O.; Tomasi, J.; Barone, V.; Cossi, M.; Cammi, R.; Mennucci, B.; Pomelli, C.; Adamo, C.; Clifford, S.; Ochterski, J.; Petersson, G. A.; Ayala, P. Y.; Cui, Q.; Morokuma, K.; Malick, D. K.; Rabuck, A. D.; Raghavachari, K.; Foresman, J. B.; Cioslowski, J.; Ortiz, J. V.; Stefanov, B. B.; Liu, G.; Liashenko, A.; Piskorz, P.; Komaromi, I.; Gomperts, R.; Martin, R. L.; Fox, D. J.; Keith, T.; Al-Laham, M. A.; Peng, C. Y.; Nanayakkara, A.; Gonzalez, C.; Challacombe, M.; Gill, P. M. W.; Johnson, B. G.; Chen, W.; Wong, M. W.; Andres, J. L.; Head-Gordon, M.; Replogle E. S.; Pople, J. A.; Gaussian, Inc., Pittsburgh Pa., 1998. A double-ζ quality basis set was used to describe C, N, O, and H (6-31 G) and a double-ζ quality basis set with a polarization function was used to describe S (6-31G*). Hehre, W. J.; Ditchfield, R.; Pople, J. A. J. Chem. Phys. 1972, 56, 2257; Francl, M. M.; Petro, W. J.; Hehre, W. J.; Binkley, J. S.; Gordon, M. S.; DeFrees, D. J.; Pople, J. A. J. Chem. Phys. 1982, 77, 3654.

Example 4

Trichloroethyl ester 5

To a stirred solution of 6-oxoheptanoic acid (2.0 g, 12.58 mmol) in benzene (40 mL) was added trichloroethanol (1.08 mL, 11.32 mmol) and $SOCl_2$ (1.1 mL, 15.1 mmol). The solution was refluxed for 8 h and then evaporated and diluted with 30 mL of EtOAc. The layers were separated and the aqueous layer was extracted with EtOAc. The combined organic layers were washed with brine, dried over $MgSO_4$ and concentrated in vacuo. Purification of the residue by flash column chromatography on $SiO_2$ eluting with EtOAc:hexanes (20:80) gave 2.1 g (61%) of ester 5 as a light yellow oil: H NMR (300 MHz, $CDCl_3$) δ4.71(s, 2H), 2.46–2.42 (m, 4H), 2.11 (s, 3H), 1.65–1.62 (m, 4H); C NMR (75 MHz, $CDCl_3$) δ 208.4, 171.8, 95.6, 74.1, 43.2, 33.8, 30.1, 24.3, 23.2; IR (neat) 2956, 1762, 1720 $cm^{-1}$.

Example 5

α-Bromoketo Ester 6

To a cooled (0° C.), stirred solution of 6-oxoheptanoic ester (1.00 g, 3.62 mmol) in CHCl$_3$ (20 mL) was slowly added bromine (0.20 mL, 3.98 mmol) in CCl$_4$ over a 1 h period and the solution was stirred at 0° C. for 3 h. The reaction mixture was diluted with 30 mL of CH$_2$Cl$_2$. The organic layer was washed with satd. aqueous NaHCO$_3$ solution, brine, and then dried over MgSO$_4$ and concentrated in vacuo. Rapid purification of the residue by flash column chromatography on SiO$_2$ eluting with EtOAc:hexanes (10:90) gave 465 mg (36%) of α-bromoester 6 as a yellow oil:H NMR (300 MHz, CDCl$_3$) δ4.78 (s, 2H), 3.92 (s, 2H), 2.79–2.72 (m, 2H), 2.59–2.48 (m, 2H), 1.81–1.71 (m, 4H)); C NMR (75 MHz, CDCl$_3$) δ 201.7, 171.7, 95.2, 74.1, 39.4, 34.4, 33.8, 24.2, 23.2; IR (neat) 2934, 1753, 1710 cm$^{-1}$; HRMS (ESI) Calcd for C$_9$H$_{12}$BrCl$_3$O$_3$ [M+H]: 376.8903 Found: 376.8901. Schreiber, S. L.; Hung, D. T.; Jamison, T. F. Chem. Biol. 1996, 3, 623–639.

Example 6

Thiazole 9

To a cooled (–5° C.), stirred solution of α-bromoketo ester 6 (354 mg, 1.0 mmol) in CH$_2$Cl$_2$ (20 mL) was added 2,6-lutidine (0.232 mL, 2.0 mmol) and thioamide 7 (380 mg, 1.0 mmol). The solution was stirred at 25° C. for 12 h and then diluted with 30 mL of CH$_2$Cl$_2$. The organic layer was washed with brine, dried over MgSO$_4$ and concentrated in vacuo. Rapid purification of the residue by flash column chromatography on SiO$_2$ eluting with EtOAc:hexanes (20:80) gave 528 mg of the intermediate thiazoline 8 as a colorless oil and as a mixture of diastereomers which was used directly in the next step. Some spectral data is provided: H NMR (300 MHz, CDCl$_3$) δ 5.91 (dt, J=1.8, 9 Hz, 1H), 4.82–4.77 (m, 1H), 4.77(s, 2H) 3.29 (s, 2H), 2.91–2.81 (m, 2H), 2.72 (ddd, J=7.2, 8.7, 14.1, 1H), 2.53 (t, J=7.5 Hz, 2H), 2.29 (s, 2H), 1.89 (t, J=9.3 Hz, 2H), 1.78 (t, J=7.2 Hz, 2H), 1.63–1.48 (m, 4H); C NMR (75 MHz, CDCl$_3$) δ 172.1, 134.9, 108.5, 74.1, 68.9, 68.6, 43.6, 43.5, 43.4, 43.2, 40.9, 34.1, 25.2, 24.7, 23.7, 18.3. 18.1, 12.5. To a cooled (0° C.), stirred solution of thiazoline (528 mg, 0.807 mmol) in CH$_2$Cl$_2$ (10 mL) was added Hünig's base (1.26 mL, 7.26 mmol), pyridine (200 μL, 2.42 mmol) and TFAA (341 μL, 2.42 mmol) and the solution was stirred at 25° C. for 3 h and then diluted with 30 mL of CH$_2$Cl$_2$. The organic layer was washed with satd. aqueous NaHCO$_3$, brine, dried over MgSO$_4$ and concentrated in vacuo. Purification of the residue by flash column chromatography on SiO$_2$ eluting with EtOAc:hexanes (20:80) gave 405 mg (80%) of thiazole 9 as a yellow oil: H NMR (300 MHz, CDCl$_3$) δ6.78 (s, 1H), 5.89 (dd, J=0.6, 8.7 Hz, 1H), 4.80 (dt, J=6.0, 9.0 1H), 4.76 (s, 2H), 3.25 (dd, J=6.3, 14.1 Hz, 1H), 3.13 (dd, J=6.3, 14.1 Hz, 1H), 2.80–2.75 (m, 2H), 2.54–2.50 (m, 2H), 2.11 (s, 3H), 1.85–1.72 (m, 4H), 1.04 (s, 21H); C NMR (75 MHz, CDCl$_3$) δ 172.1, 165.4, 156.6, 135.1, 121.5, 113.4, 95.2, 74.1, 70.3, 42.2, 33.9, 31.3, 28.8, 24.5, 24.2, 18.2, 12.5; HRMS (ESI) Calcd for C$_{24}$H$_{40}$BrCl$_3$NO$_3$SSi [M+H]: 634.0717 Found: 634.0748.

Example 7

Thiazole enyne 12

To a cooled (–20° C.), stirred solution of thiazole 8 (53 mg, 3.62 mmol) in THF (1.0 mL) was added 0.20 mL of 1M TBAF (0.20 mmol) buffered with 20 mol % AcOH and the solution was stirred at –20° C. for 3 h. The reaction mixture was diluted with 10 mL of CH$_2$Cl$_2$. The organic layer was washed with satd. aq. NaHCO$_3$, brine, dried over MgSO$_4$ and concentrated in vacuo. Crude purification of the residue by flash column chromatography on SiO$_2$ eluting with EtOAc:hexanes (20:80→50:50) gave 38 mg of alcohol 10 as a light yellow oil which was used directly in the next step. To a solution of DIAD (0.032 mL, 0.167 mmol) in THF (0.5 mL) was added PPh$_3$ (35 mg, 0.1336 mmol) as a solid and the solution was stirred at ambient temperature for 30 min. The resulting heterogeneous mixture was cooled (–20° C.) and the solution of acid (30 mg, 0.0935 mmol) in THF (0.2 mL) was added. After 20 min, a solution of alcohol (32 mg, 0.0668 mmol) in THF (0.2 mL) was added and stirring was continued for 1 h. The reaction was quenched by addition of 2 mL pH 7 buffer followed by warming to 25° C. and diluting with 20 mL of EtOAc. The layers were separated and the aqueous layer was extracted with EtOAc. The combined organic layers were washed with brine, dried over Na$_2$SO$_4$ and concentrated in vacuo. Purification of the residue by flash column chromatography on SiO$_2$ eluting with EtOAc:hexanes (10:90) gave 37 mg (71%) of thiazole enyne 12 as a light yellow oil: $^1$H NMR (300 MHz, CDCl$_3$) δ6.77 (s, 1H), 5.87 (dd, J=1.2, 9.6 Hz, 1H), 5.79–5.72 (m, 1H), 5.38 (d, J=1.2 Hz, 1H), 4.71 (s, 2H), 4.13–4.07 (m, 1H), 3.36 (dd, J=6.9, 14.7 Hz, 1H), 3.24 (dd, J=6.9, 14.7 Hz, 1H), 2.74 (t, J=6.9 Hz, 1H), 2.48 (t, J=6.9 Hz, 2H), 2.39 (dd, J=5.4, 14.7 Hz, 1H), 2.23 (dd, J=5.4, 14.7 Hz, 1H), 2.26 (d, J=1.2 Hz, 1H), 1.99 (d, J=1.5 Hz, 3H), 1.77–1.69 (m, 4H), 1.24–1.22 (m, 2H), 1.11 (d, J=6.3 Hz, 3H), 1.03 (s, 21H); HRMS (ESI) Calcd for C$_{33}$H$_{50}$BrCl$_3$NO$_5$SSi [M+H]: 784.1428 Found: 784.1434.

Example 8

Alcohol 13

To a stirred solution of silylether (30 mg, 0.038 mmol) in THF (0.5 mL) was added 20 mol % AcOH/TBAF (0.095 mL, 0.095 mmol). The resulting solution was stirred at 25° C. for 12 h. The reaction mixture was diluted with 10 mL of CH$_2$Cl$_2$. The combined organic layers were washed with satd. aqueous NaHCO$_3$, brine, dried over MgSO$_4$ and concentrated in vacuo. Purification of the residue by flash column chromatography on SiO$_2$ eluting with EtOAc:hexanes (50:50) gave 18 mg (75%) of alcohol 13 as a pale yellow oil: H NMR (500 MHz, CDCl$_3$) δ6.84 (s, 1H), 5.92 (dd, J=1.2, 6.9 Hz, 1H), 5.86–5.79 (m, 1H), 5.48 (s, 1H), 4.77 (s, 2H), 4.07–4.01 (m, 1H), 3.43 (dd, J=6.9, 14.7 Hz, 1H), 3.29 (dd, J=6.9, 14.7 Hz, 1H), 2.81 (t, J=6.6 Hz, 2H), 2.54 (t, J=6.9 Hz, 1H), 2.32 (d, J=1.5 Hz, 3H), 2.07 (d, J=1.2 Hz, 3H), 1.80–1.76 (m, 4H), 1.26 (d, J=6.3 Hz, 3H); C NMR (125 MHz, CDCl$_3$) δ 172.1, 171.4, 163.7, 158.5, 156.9, 153.2, 128.6, 128.1, 113.8, 105.2, 85.6, 83.7, 74.1, 71.6, 65.9, 48.9, 38.0, 33.9, 31.2, 28.7, 24.5, 23.6, 20.7, 14.4; HRMS (ESI) Calcd for C$_{24}$H$_{39}$BrCl$_3$NO$_5$S [M+H]: 628.0094 Found: 628.0073.

Example 9

Macrocycle 15

To a stirred solution of alcohol 13 (10 mg, 0.0158 mmol) in THF (0.2 mL) and 1M NH$_4$OAc (0.2 mL) was added 10% Cd/Pd couple (5.0 mg) The resulting solution was stirred at 25° C. for 2 h. The reaction mixture was diluted with 10 mL of EtOAc and then filtered through a celite pad. The organic layer was washed with brine, dried over MgSO$_4$ and concentrated in vacuo. The crude hydroxy acid 14 was submitted directly to macrocyclization conditions without purification. To a cooled (0° C.) stirred solution of hydroxy acid 14 (8 mg, 0.016 mmol) in THF (0.5 mL) was added Et$_3$N (13 µL, 0.096 mmol) and 2,4,6-trichlorobenzoyl chloride (12.5 µL, 0.08 mmol). The resulting solution was stirred at 0° C. for 20 min and then added to a solution of DMAP (19.5 mg, 0.16 mmol) in toluene (8 mL) at 25° C. and stirred for 2 h. The reaction mixture was diluted with 10 mL of EtOAc. The organic layer was washed with brine, dried over MgSO$_4$ and concentrated in vacuo. Purification of the residue by flash column chromatography on SiO$_2$ eluting with EtOAc:hexanes (30:70) gave 7.0 mg (92%, 2 steps) of macrocycle 15 as a pale yellow oil: H NMR (300 MHz, CDCl$_3$) δ6.82 (s, 1H), 6.06 (dd, J=1.2, 9.3 Hz, 1H), 5.93–5.86 (m, 1H), 5.35 (s, 1H), 5.33–5.26 (m, 1H), 3.34 (br d, J=7.5 Hz, 2H), 2.81–2.61 (m, 2H), 2.46–2.39 (m, 1H), 2.43 (d, J=1.5 Hz, 3H), 2.30 (d, J=6.9 Hz, 2H), 1.96 (d, J=1.2 Hz, 3H), 1.90–1.68 (m, 3H), 1.57–1.45 (m, 3H), 1.28 (d, J=6.3 Hz, 3H); HRMS (ESI) Calcd for C$_{22}$H$_{27}$BrCl$_3$NO$_4$S [M+H]: 480.0844 Found: 480.0760.

Example 10

DMDA PatA (3)

A slurry of Pd/CaCO$_3$ poisoned with Pb (5.0 mg) and macrocycle 15 (5.0 mg, 0.0104 mmol) in 0.3 mL of MeOH was evacuated under water aspirator pressure and purged with H$_2$. After stirring at 25° C. for 12 h under 1 atm of H$_2$, the reaction was filtered through Celite, concentrated in vacuo. Passage through a plug of SiO$_2$ eluting with EtOAc:hexanes (50:50) gave 4.6 mg (92%) of E,Z-macrocycle 16 as a colorless oil: H NMR (300 MHz, CDCl$_3$) δ7.02 (d, J=11.7 Hz, 1H), 6.72 (s, 1H), 6.71 (dd, J=11.7 Hz, 1H), 6.08 (dt, J=4.5, 16.5 Hz, 1H), 5.97 (dq, J=1.2, 9.6 Hz, 1H), 5.36 (d, J=11.7 Hz, 1H), 5.23–5.12 (m, 1H), 3.27–3.14 (m, 2H), 2.93–2.83 (m, 1H), 2.60 (ddd, J=4.5, 10.5, 1.4 Hz, 1H), 2.53–2.47 (m, 1H), 2.51 (s, 3H), 2.41–2.13 (m, 4H), 1.86 (s, 3H), 1.77–1.61 (m, 2H), 1.44–1.29 (m, 2H), 1.27 (d, J=6.6 Hz, 3H). This material was directly used in the next reaction without further purification. To a flask charged with Pd$_2$dba$_3$.CHCl$_3$ (1.7 mg, 0.0016 mmol) and triphenyl arsine (4.1 mg, 0.013 mmol) was added 0.1 mL of degassed THF prepared by several freeze/thaw cycles. The final concentration of this palladium catalyst stock solution was ~0.031 M. To a solution of macrocycle 16 (4.0 mg, 0.0083 mmol) and stannane 17 (7.0 mg, 0.0166 mmol) in 0.1 mL of THF was added 0.027 mL (0.000837 mmol, 10 mol %) of palladium catalyst stock solution. The resulting solution was stirred at 25° C. for 2 h and concentrated in vacuo. Purification of the residue by flash column chromatography on SiO$_2$ eluting with EtOAc:hexanes:Et$_3$N (45:52:8) gave 2.1 mg (49%) of DMDAPatA (3) as a pale yellow oil: H NMR (500 MHz, C$_6$D$_6$) δ 7.47 (d, J=12.0 Hz, 1H), 6.71 (app dt, J=5.0, 9.0 Hz, 1H), 6.45 (app t, J=11.5 Hz, 1H), 6.32 (d, J=16.0 Hz, 1H), 6.21 (d, J=16.0 Hz, 1H), 6.17 (s, 1H), 5.69 (t, J=7 Hz, 1H), 5.55 (d, J=11.5 Hz, 1H), 5.49 (d, J=9.0 Hz, 1H), 5.19–5.11 (m, 1H), 3.08–3.01 (m, 2H), 2.91 (d, J=6.5 Hz, 2H), 2.78 (dt, J=4.5, 14.0 Hz, 1H), 2.48–2.42 (m, 1H), 2.33 (ddd, J=4.0, 10.0, 14.5 Hz, 1H), 2.11 (s, 6H), 2.16–2.03 (m, 2H), 1.90 (d, J=1.0 Hz, 3H), 1.71 (2, 3H), 1.64–1.61 (m, 1H), 1.56–1.43 (m, 2H), 1.54 (s, 3H), 0.96–0.81 (m, 2H), 0.95 (d, J=6.5 Hz, 3H); HRMS (ESI) Calcd for C$_{30}$H$_{43}$N$_2$O$_4$S [M+H]: 527.2944 Found: 527.2927.

The complete content of all publications, patents and patent applications cited in this description are herein incorporated by reference as if each individual publication, patent or patent application.

The foregoing invention has been described above in some detail by way of illustration and example for the purposes of clarity of understanding. The above examples are provided for exemplification purposes only and are not intended to limit the scope of the invention, which has been described in broad terms before the examples. It will be readily apparent to one skilled in the art in light of the teachings of this invention that changes and modifications can be made without departing from the spirit and scope of the present invention.

What is claimed is:

1. A compound of the formula:

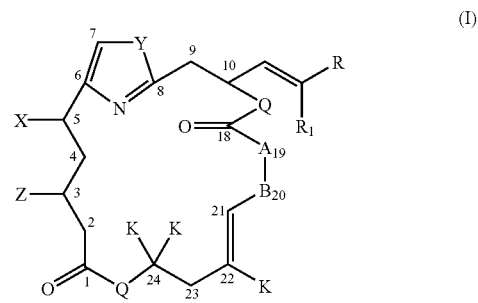

(I)

and its pharmaceutically accepted salts, wherein

A—B is ethane, (E) and (Z)-ethene, (E) and (Z)-substituted ethene, ethyne,

K is hydrogen or one-to-three carbon alkyl group,

Q=NH or O,

X is hydrogen, hydroxy, alkoxy, alkyl, aminocarbonyl, amino, alkylamino, dialkylamino, alkoxycarbonylamino, Y is S, NH, or O, Z is hydrogen, hydroxy, aminocarbonyl, alkylamino, dialkylamino, alkoxycarbonylamino, but not t-butoxycarbonylamino when R$_4$ is dimethylamino, R$_1$ is hydrogen or one-to-three carbon alkyl group, and R is selected from the following:

(a) Alkene of the formula:

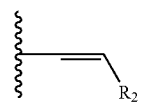

wherein R$_2$ is optionally substituted with one or more substituents selected from alkyl, alkylhydroxy, alkylalkoxy, alkylamino, alkylaminoalkyl, or alkylaminodialkyl;

(b) Alkenylaryl of the formula:

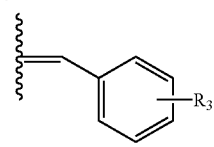

wherein $R_3$ is optionally substituted with one or more substituents selected from hydrogen, alkyl, alkenyl, alkynyl, hydroxy, alkoxy, amino, alkylamino, dialkylamino, trifluoromethane, or fluoro; and (c) Methyldienylpentyl of the formula:

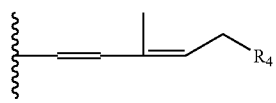

wherein $R_4$ is optionally substituted with one or more substituents selected from hydrogen, alkyl, alkenyl, alkynyl, hydroxy, alkoxy, amino, alkylamino, or dialkylamino; and (d) Methylalkenylpentyl of the formula:

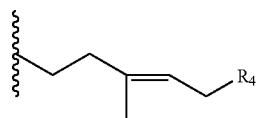

wherein $R_4$ is optionally substituted with one or more substituents selected from hydrogen, alkyl, alkenyl, alkynyl, hydroxy, alkoxy, amino, alkylamino, or dialkylamino.

2. A compound of the formula:

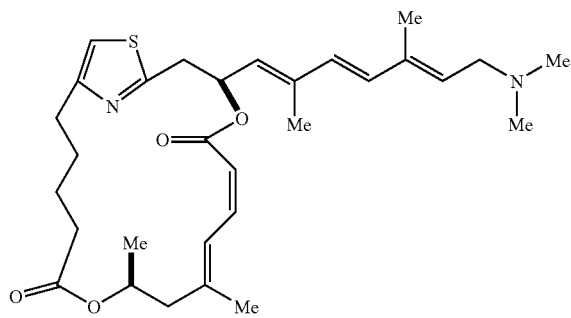

and its pharmaceutically accepted salts.

3. A compound of the formula:

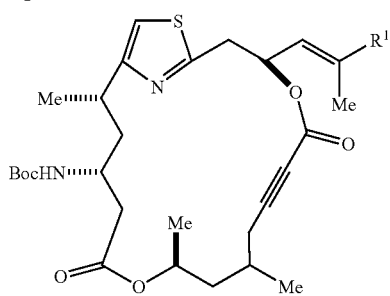

and its pharmaceutically accepted salts, wherein $R^1$ is selected from hydroxyalkene, methoxyalkene, dimethyl amino alkene; and dimethyl amino methyldiene.

4. A compound of the formula:

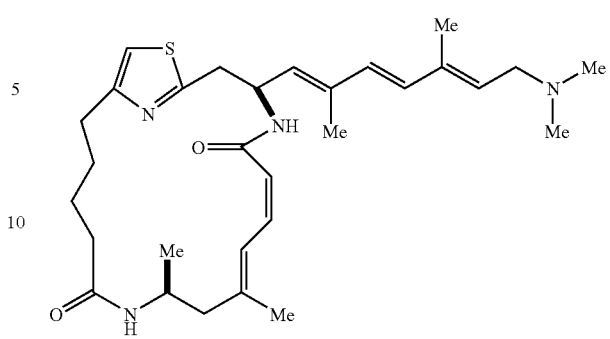

and its pharmaceutically accepted salts.

5. A compound of the formula:

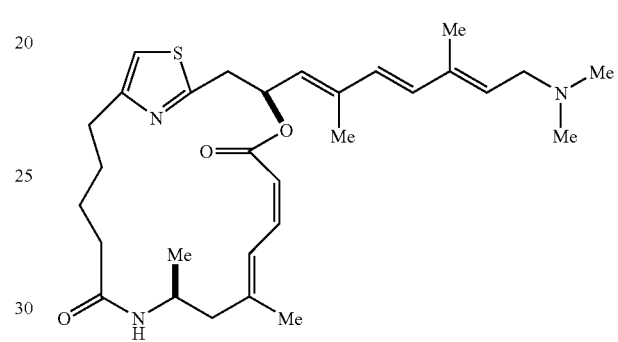

and its pharmaceutically accepted salts.

6. A compound of the formula:

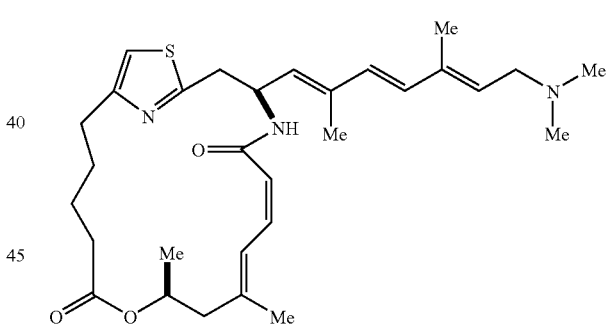

and its pharmaceutically accepted salts.

7. A compound of the formula:

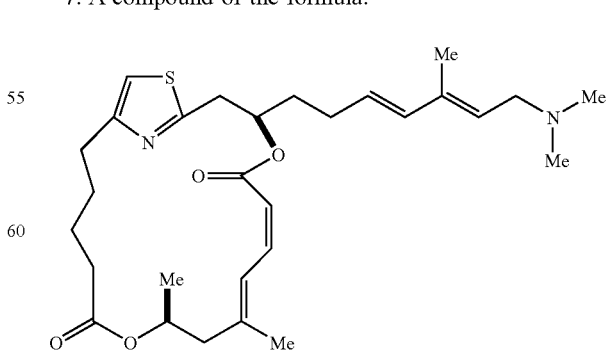

and its pharmaceutically accepted salts.

8. A compound of the formula:

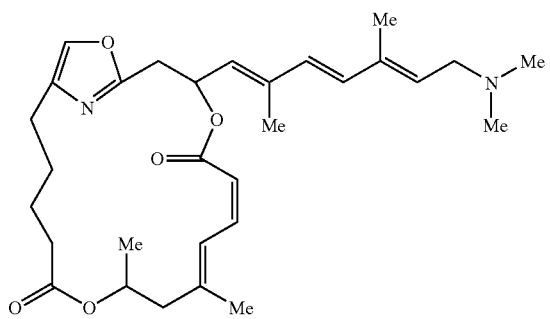

and its pharmaceutically accepted salts.

9. A compound of the formula:

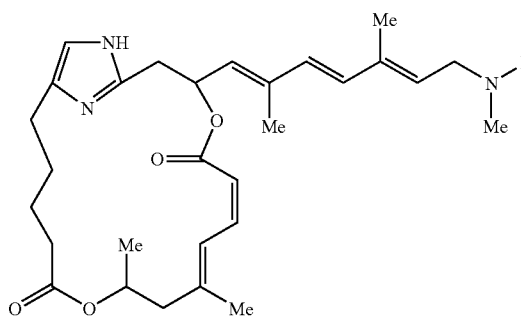

and its pharmaceutically accepted salts.

10. A compound of the formula:

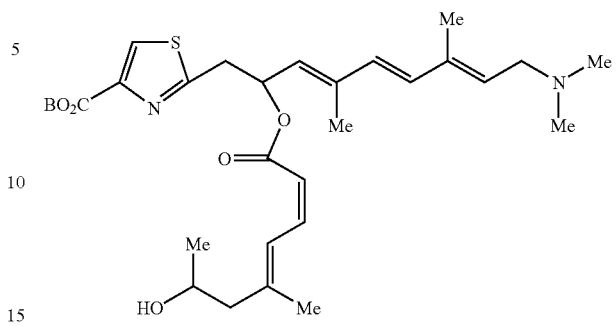

and its pharmaceutically accepted salts.

11. A compound of the formula:

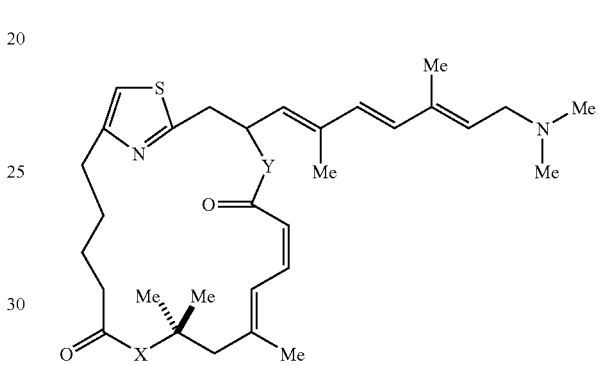

and its pharmaceutically accepted salts, wherein
X=O, NH or NR; and
Y=O, NH or NR, where R is alkyl or aryl group.

12. A method of making a biotinylated derivative of PatA, comprising the steps of:

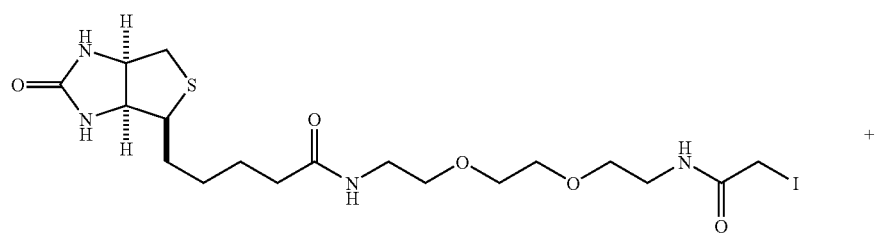

Biotin-PEO-Iodide

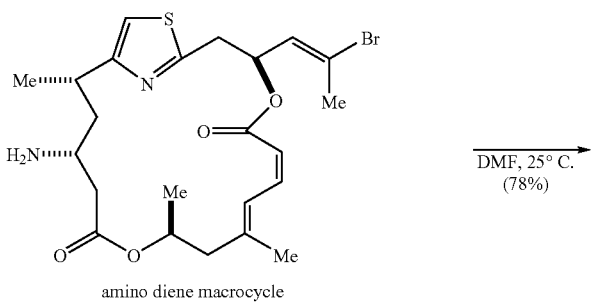

amino diene macrocycle

-continued
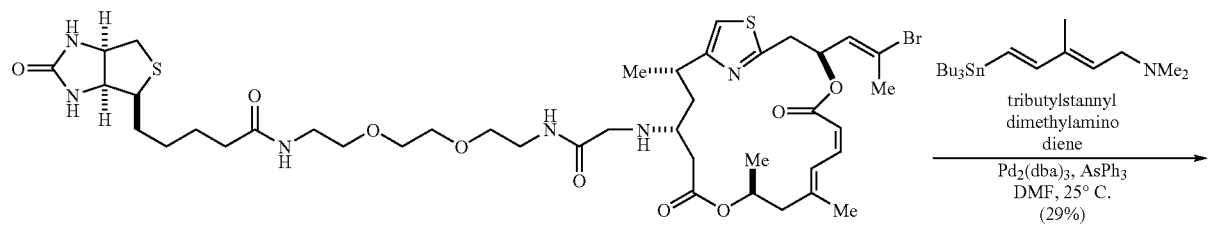
Biotin-PEO-diene macrocycle
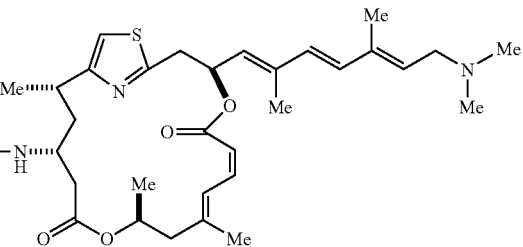
Biotin-PEO-Pateamine A
13. A method of synthesis of DMDA Pat A comprising the steps of:
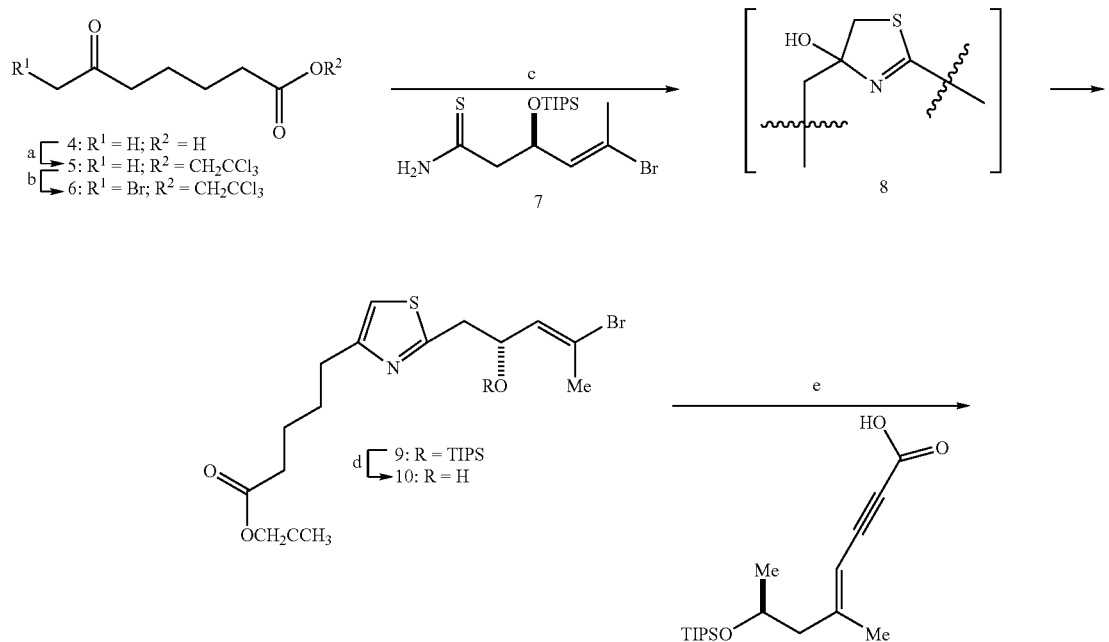

-continued

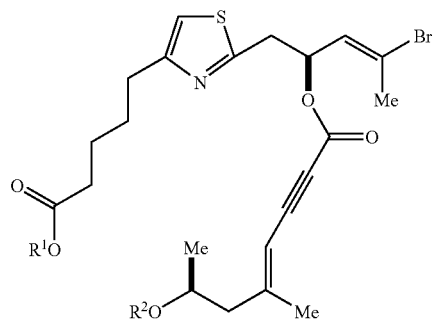

d ⎡ 12: R¹ = CH₂CCl₃; R² = TIPS
  ⎣→ 13: R¹ = CH₂CCl₃; R² = H
f  → 14: R¹ = H; R² = H

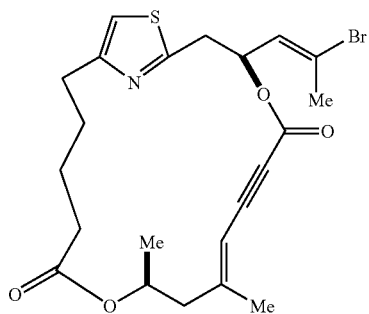

15

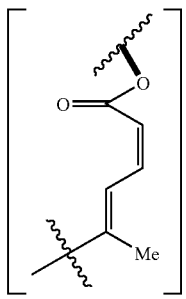

16

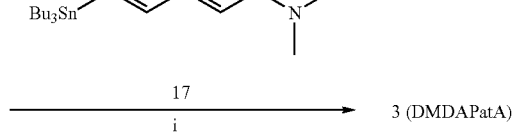

3 (DMDAPatA)

, wherein a indicates treatment with trichloroethanol and thionyl chloride in benzene at reflux for 5 hours; b indicates treatment with bromine in a chloroform/carbon tetrachloride co-solvent mixture at 0 degrees C. for 3 hours; c indicates treatment with 2,6-lutidine in dichloromethane at 25 degrees C. for 12 hours followed by trifluoroacetic anhydride, pyridine and Hünig's base from 0 to 25 degrees C. for 3 hours; d indicates treatment with tetrabutylammonium fluoride and 20 mol % acetic acid in tetrahydrofuran at −20 degrees C. for 1 hour for compound 10 and 25 degrees C. for 12 hours for compound 13; e indicates treatment with a triphenylphosphine and diisopropyl azodicarboxylate in tetrahydrofuran at −20 degrees C. for 2 hours; f indicates treatment with 10% cadmium/lead couple in tetrahydrofuran/1M ammonium acetate at 25 degrees C. for 2 hours; g indicates treatment with 2,4,6-trichlorobenzoyl chloride, triethylamine and dimethylaminopyridine in toluene/tetrahydrofuran (0.001 M) co-solvent mixture at 25 degrees C. for 2 hours; h indicates treatment with palladium with calcium carbonate poisoned with lead and hydrogen gas in methanol at 25 degrees C. for 12 hours; and indicates treatment with 10 mol % [palladium dibenzylidene acetone.chloroform complex:arsine in 1:8 ratio] and compound 17 in tetrahydrofuran at 25 degrees C. for 2 hours.

* * * * *